(12) United States Patent
Oka et al.

(10) Patent No.: US 6,294,547 B1
(45) Date of Patent: Sep. 25, 2001

(54) NAPHTHYRIDINE DERATIVES OR SALTS THEREOF

(75) Inventors: Hiroko Oka, Tokyo; Masashi Iida, Kitamoto; Yoshitaka Sato, Yoshikawa; Maki Honda, Hasuda, all of (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/446,452

(22) PCT Filed: Jun. 30, 1998

(86) PCT No.: PCT/JP98/02921

§ 371 Date: Dec. 21, 1999

§ 102(e) Date: Dec. 21, 1999

(87) PCT Pub. No.: WO99/00388

PCT Pub. Date: Jan. 7, 1999

(30) Foreign Application Priority Data

Jun. 30, 1997 (JP) .................................... 9-187274
May 19, 1998 (JP) ................................. 10-136225

(51) Int. Cl.[7] ................. C07D 471/04; A61K 31/4375
(52) U.S. Cl. ............................... 514/292; 546/81
(58) Field of Search ............................ 514/292; 546/81

(56) References Cited

U.S. PATENT DOCUMENTS

| 3,555,034 | 1/1971 | Diebold et al. ................. 260/295 |
| 4,647,566 | 3/1987 | Yokoyama ....................... 514/293 |
| 5,346,904 | 9/1994 | Flockerzi et al. ................. 514/292 |

FOREIGN PATENT DOCUMENTS

| 2087390 | * 10/1981 | (GB) . |
| 57-75983 | 5/1982 | (JP) . |
| 58-57379 | 4/1983 | (JP) . |

* cited by examiner

Primary Examiner—Mukund J. Shah
Assistant Examiner—Deepak R. Rao
(74) Attorney, Agent, or Firm—Nields & Lemack

(57) ABSTRACT

A novel naphthyridine compound represented by the general formula (1):

$$R^1 \diagup N \diagdown \diagdown \diagdown \diagdown N-X-\underset{Z}{\overset{\text{CH}}{|}}-Y-N\diagdown\genfrac{}{}{0pt}{}{A}{G}$$
$$R^2 \diagdown \diagup \diagup R^3$$

(I)

wherein $R^1$, $R^2$ and $R^3$ are independently a hydrogen atom, a lower alkyl group or the like, or $R^1$ and $R^2$, or $R^2$ and $R^3$, when taken together, form a cyclic group; each of X and Y is a methylene or ethylene group; Z is a phenyl group, a substituted phenyl group or the like; A is a hydrogen atom, a lower alkyl group or the like; and G is an acyl group, shows antagonism for tachykinin receptors and is useful as a prophylactic or therapeutic agent for diseases for which the tachykinin receptors are considered to be responsible. A specific example of such a compound is 2-[(−)-4-(N-benzoyl-N-methyl)amino-3-(3,4-dichlorophenyl)butyl]-10-acetylamino-1,2,3,4-tetrahydro-benzo[b][1,6]naphthyridine.

16 Claims, No Drawings

NAPHTHYRIDINE DERATIVES OR SALTS THEREOF

This application is a 371 of PCT/JP98/02921 filed Jun. 30, 1998.

1. TECHNICAL FIELD

The present invention relates to novel naphthyridine compounds capable of showing antagonism for tachykinin receptors, in particular, antagonism for neurokinin A receptors (NK-2 receptors); salts thereof, hydrates thereof or solvates thereof; and pharmaceutical compositions containing said compounds. The compounds of the present invention are useful as prophylactic or therapeutic agents for diseases for which tachykinin receptors are considered to be responsible, such as asthma, bronchitis, pollakiuria, urinary incontinence and colitis.

2. BACKGROUND ART

The term "tachykinins" is a general term for a group of peptides having similar structures, which are neuropeptides widely present in nervous system. Tachykinins participate in olfaction, vision, audition, movement control, gastric movement, and salivation control. In addition, it has recently become apparent that tachykinins also have other various physiological actions such as contraction of respiratory tract smooth muscle, contraction of bladder smooth muscle, contraction of intestinal tract smooth muscle, induction of airway hyperresponsiveness, increase in vascular permeability, cough induction, pain infliction, mucus hypersecretion, edema induction, vasodilation, vomitting induction, diuresis acceleration, anxiety symptom induction, macrophage activation, mast cell activation, etc. Therefore, there has been suggested possibility that antagonists against tachykinins may become effective therapeutic agents for diseases whose pathosis deeply involve the above-mentioned actions, such as asthma, bronchitis, pneumonia, chronic obstructive pulmonary disease, pollakiuria, urinary incontinence, colitis, diabetes, central diseases, various pains, allergic disease, rheumatoid arthritis, osteoarthritis, various inflammations, etc. As typical tachykinins derived from mammals, there are substance P, neurokinin A and neurokinin B. There are also N-terminal extension subtypes of neurokinin A.

For these three main tachykinins, at least three receptors are known. According to the relative selecting properties of these receptors having affinity for substance P, neurokinin A or neurokinin B, respectively, the receptors are classified into neurokinin-1 (NK-1) receptor, neurokinin-2 (NK-2) receptor and neurokinin-3 (NK-3) receptor. Through these receptors, tachykinins exhibit widely various physiological actions. It is known that NK-2 receptors participate in airflow limitation in asthma [Bertrand, C. et al., Am. J. Physiol. 265, L507–L511 (1993); Perretti, F. et al., Eur. J. Pharmacol. 273, 129–135 (1995)]. In addition, it is known that NK-2 receptors participate also in airway hyperresponsiveness in asthma and that antagonists at NK-2 receptors inhibit the hyper-responsiveness substantially completely [Biochot, E. et al., Br. J. Pharmacol. 114, 259–261 (1995)]. It is also known that the antagonists at NK-2 receptors inhibit the release of a chemical mediator from lungs by antigen challenge [Ciabattoni, G. et al., Pharmacodyn. Ther. 328, 357–358 (1994)] and also suppress airway edema in asthma [Tousignant C., et al., Br. J. Pharmacol. 108, 383–386 (1993)]. Further, it has been revealed by clinical experiments that antagonists at NK-1 and NK-2 receptors protected the bronchoconstriction induced by bradykinin in asthmatic patients [Ichinose, M. et al., Lancet 340, 1248–1251 (1992)].

Thus, it is known that the antagonists at NK-2 receptors are useful as a prophylactic or therapeutic agent for asthma. It is also known that the antagonists at NK-2 receptors and antagonists at NK-1 receptors are useful also as an antitussive in the case of bronchitis, etc [Advenier, C. et al., Eur. J. Pharmacol. 250, 169–171 (1993); Yasumitsu, R. et al. Eur. J. Pharmacol. 300, 215–219 (1996)]. The antagonists at NK-2 receptors are considered to be useful as a prophylactic and therapeutic agent for pollakiuria and urinary incontinence [Croci, T. et al., J. Pharm. Pharmacol. 46, 383–385 (1994); Palea S., et al., J. Pharm. Exp. Ther. 277, 700–705 (1996)]. In addition, they are considered to be hopeful as a prophylactic and therapeutic agent for colitis [Maggi, C. A. et al., Drugs of the Future 18, 155–158 (1993)]. It is known that NK-2 receptor participates in various pains [Santucci, V. et al., Eur. J. Pharmacol. 237, 143–146 (1993); Wiesenfeld-Hallin, Z. et al., Eur. J. Pharmacol. 251, 99–102 (1994)] and inflammations [Lam F.Y. et al., Br. J. Pharmacol. 118, 2107, 2114 (1996)] and that the antagonists at NK-2 receptors suppress the pains and inflammations. It is known that NK-2 receptors participate also in central diseases such as anxiety [S. C. Stratton et al., Br. J. Pharmacol. 112 (supplement) 49p (1993)]. Further, it has been reported that the antagonists at NK-1 receptors markedly suppress experimental vomiting caused by chemotherapeutic drugs such as cisplatin, analgesics such as morphine, and X-ray irradiation, etc. [Bountra, C. et al., Eur. J. Pharmacol. 249, R3–R4 (1993), Tatterall, F. D. et al., Eur. J. Pharmacol. 250, R5–R6 (1993)].

Compounds antagonistic to tachykinins at the tachykinin receptors of the above-mentioned types have been reported. For example, Japanese Patent Unexamined Publication No. 4-261155 discloses compounds capable of showing antagonism for neurokinin receptors (in particular, NK-2 receptor). In addition, Japanese Patent Unexamined Publication No. 5-140103 discloses compounds capable of showing antagonism for substance P receptor, neutokinin A receptor or neurokinin B receptor. These compounds have a single ring containing at least one nitrogen atom. From these compounds, the compounds of the present invention are structually and strikingly different in that they have a naphthyridine ring as shown in the chemical formula (1) described hereinafter. On the other hand, various compounds having a naphthyridine ring are also known. For example, Japanese Patent Unexamined Publication No. 58-57379 discloses naphthyridine compounds having antidinic effect. However, it has not been reported at all that these compounds show antagonism for a tachykinin receptor.

DISCLOSURE OF THE INVENTION

An object of the present invention is to provide novel naphthyridine compounds, a process for producing them, and pharmaceutical compositions containing them as an active ingredient.

In particular, the present invention is intended to provide naphthyridine compounds used for preventing or treating pathological phenomena caused by tachykinins and diseases caused by tachykinins.

The present inventors found that novel naphthyridine derivatives represented by the general formula (1) and pharmaceutically acceptable salts thereof are antagonistic to tachykinins, whereby the present invention has been accomplished.

That is, the present invention relates to the following items (1) to (15).

(1) A novel naphthyridine derivative represented by the following general formula (1):

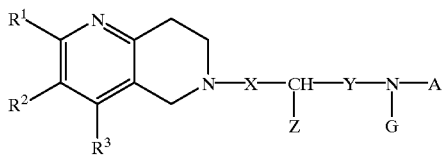

wherein $R^1$, $R^2$ and $R^3$ are independently selected from the group consisting of hydrogen atom; lower alkyl groups; halogeno-lower-alkyl groups; aryl groups; heteroaryl groups; lower alkoxy groups; hydroxyl group; amino group; halogen atoms; trifluoromethyl group; amino protecting groups represented by $NR_aCOR_b$ wherein $R_a$ and $R_b$ are independently a hydrogen atom, a lower alkyl group, a cycloalkyl group, an aryl group or a heteroaryl group; lower acyloxy groups; nitro group; cyano group; amino protecting groups represented by $NR_aR_b$ wherein $R_a$ and $R_b$ are independently a hydrogen atom, a lower alkyl group, a cycloalkyl group, an aryl group or a heteroaryl group; lower alkylsulfonylamino groups; lower alkoxycarbonyl groups; carboxyl group; lower acyl groups; carbamoyl group; aminocarbonyl groups represented by $CONR_aR_b$ wherein $R_a$ and $R_b$ are independently a hydrogen atom, a lower alkyl group, a cycloalkyl group, an aryl group or a heteroaryl group; aminocarbonyl groups represented by $COJ$ wherein $J$ is a substituted or unsubstituted pyrrolidino, piperidino, piperazino, homopiperazino or morpholino group; lower alkylsulfonyl groups; amino protecting groups represented by $NR_aCOOR_b$ wherein $R_a$ and $R_b$ are independently a hydrogen atom, a lower alkyl group, a cycloalkyl group, an aryl group or a heteroaryl group; and hydroxyl-lower-alkyl groups, or a combination of $R^1$ and $R^2$ or a combination of $R^2$ and $R^3$ forms through the saturated or unsaturated carbon-carbon bond a cyclic group which may contain 1 to 3 heteroatoms selected from nitrogen atom, oxygen atom and sulfur atom and may have a substituent selected from the group consisting of lower alkyl groups; aryl groups; heteroaryl groups; lower alkoxy groups; hydroxyl group; amino group; halogen atoms; trifluoromethyl group; amino protecting groups represented by $NR_aCOR_b$ wherein $R_a$ and $R_b$ are independently a hydrogen atom, a lower alkyl group, a cycloalkyl group, an aryl group or a heteroaryl group; lower acyloxy groups; nitro group; cyano group; amino protecting groups represented by $NR_aR_b$ wherein $R_a$ and $R_b$ are independently a hydrogen atom, a lower alkyl group, a cycloalkyl group, an aryl group or a heteroaryl group; lower alkylsulfonylamino groups; lower alkoxycarbonyl groups; carboxyl group; lower acyl groups; carbamoyl group; aminocarbonyl groups represented by $CONR_aR_b$ wherein $R_a$ and $R_b$ are independently a hydrogen atom, a lower alkyl group, a cycloalkyl group, an aryl group or a heteroaryl group; aminocarbonyl groups represented by $COJ$ wherein $J$ is a substituted or unsubstituted pyrrolidino, piperidino, piperazino, homopiperazino or morpholino group; lower alkylsulfonyl groups; oxo group; amino protecting groups represented by $NR_aCOOR_b$ wherein $R_a$ and $R_b$ are independently a hydrogen atom, a lower alkyl group, a cycloalkyl group, an aryl group or a heteroaryl group; and hydroxyl-lower-alkyl groups, X and Y are independently a methylene chain represented by $—(CH_2)_n—$ wherein n is 0 to 3, Z is a hydrogen atom, a lower alkyl group, a lower alkenyl group, a cycloalkyl group, an aryl group, an arylalkyl group, an arylalkenyl group, a heteroaryl group, a heteroarylalkyl group or a heteroarylalkenyl group, each of which may have one or more substituents selected from the group consisting of lower alkyl groups, aryl groups, heteroaryl groups, lower alkoxy groups, hydroxyl group, amino group, halogen atoms and trifluoromethyl group, A is a hydrogen atom, a lower alkyl group or a lower alkoxy group, and G is a hydrogen atom, a lower alkyl group, a lower alkoxy group, an arylalkyl group or an acyl group represented by $—C(=O)XZ$, $—C(=O)CH(R^1)(Z)$ or $—C(=O)C(R^1)(R^2)(Z)$ wherein X, Z, $R^1$ and $R^2$ are as defined above, or a pharmacologically acceptable salt thereof.

(2) A compound or a pharmacologically acceptable salt thereof according to the above item 1, wherein $R^1$, $R^2$ and $R^3$ are independently a hydrogen atom, a lower alkyl group, an aryl group, an amino group, a halogen atom, an amino protecting groups represented by $NR_aCOR_b$ wherein $R_a$ and $R_b$ are as defined above, a lower alkoxycarbonyl group, a carboxyl group, a carbamoyl group, an amino protecting groups represented by $NR_aCOOR_b$ wherein $R_a$ and $R_b$ are as defined above, or a hydroxyl-lower-alkyl group, or a combination of $R^1$ and $R^2$ or a combination of $R^2$ and $R^3$ forms a cyclic group which may contain 1 to 3 heteroatoms selected from nitrogen atom, oxygen atom and sulfur atom, through the saturated or unsaturated carbon-carbon bond, provided that at least one of $R^1$, $R^2$ and $R^3$ is a lower alkyl group when neither of the combinations forms a cyclic group; X is a methylene chain represented by $—(CH_2)_2—$; Y is a methylene chain represented by $—CH_2—$; and Z is a phenyl group, a thienyl group, an imidazolyl group, a pyridinyl group, a pyrimidinyl group, a pyridazinyl group, biphenyl group or a naphthyl group, which may have 1, 2 or 3 substituents selected from lower alkyl groups and halogen atoms.

(3) A compound or a pharmacologically acceptable salt thereof according to the above item 1, wherein $R^1$, $R^2$ and $R^3$ are independently a hydrogen atom, a lower alkyl group, an aryl group, an amino group, a halogen atom, an amino protector represented by $NR_aCOR_b$ wherein $R_a$ and $R_b$ are as defined above, a lower alkoxycarbonyl group, a carboxyl group, a carbamoyl group, an amino protecting groups represented by $NR_aCOOR_b$ wherein $R_a$ and $R_b$ are as defined above, or a hydroxyl-lower-alkyl group, or $R^1$ and $R^2$, or $R^2$ and $R^3$, when taken together, form a $C_2$–$C_5$ alkylene group or a $C_2$–$C_5$ alkenylene group, provided that at least one of $R^1$, $R^2$ and $R^3$ is a lower alkyl group when neither of the combinations forms a ring; Z is a phenyl group which may have 1, 2 or 3 substituents selected from halogen atoms; A is a hydrogen atom, a $C_1$–$C_4$ lower alkyl group or a $C_1$–$C_4$ lower alkoxy group; and G is a benzoyl group which may have 1, 2 or 3 substituents selected from halogen atoms and lower alkoxy groups.

(4) A compound or a pharmacologically acceptable salt thereof according to the above item 1, wherein $R^1$, $R^2$ and $R^3$ are independently a hydrogen atom, a lower alkyl group, an aryl group, an amino group, an amino protecting groups represented by $NR_aCOR_b$ wherein $R_a$ and $R_b$ are as defined above, a lower alkoxycarbonyl group, a carbamoyl group, or an amino protecting groups represented by $NR_aCOOR_b$ wherein $R_a$ and $R_b$ are as defined above, or $R^1$ and $R^2$, or $R^2$ and $R^3$, when taken together, form a $C_2$–$C_5$ alkylene group or a $C_2$–$C_5$ alkenylene group, provided that at least one of $R^1$, $R^2$ and $R^3$ is a lower alkyl group when neither of the combinations forms a ring; Z is a phenyl group which may have 1, 2 or 3 substituents selected from halogen atoms; A is a hydrogen atom, a $C_1$–$C_4$ lower alkyl group or a $C_1$–$C_4$ lower alkoxy group; and G is a benzoyl group which may have 1, 2 or 3 substituents selected from halogen atoms and lower alkoxy groups.

(5) A compound or a pharmacologically acceptable salt thereof according to the above item 1, wherein $R^1$, $R^2$ and $R^3$ are independently a hydrogen atom, a lower alkyl group, an amino protecting groups represented by $NR_aCOR_b$ wherein $R_a$ and $R_b$ are as defined above, or an amino protecting groups represented by $NR_aCOOR_b$ wherein $R_a$ and $R_b$ are as defined above, or $R^1$ and $R^2$, or $R^2$ and $R^3$, when taken together, form a $C_2$–$C_5$ alkylene group or a $C_2$–$C_5$ alkenylene group, provided that at least one of $R^1$, $R^2$ and R3 is a lower alkyl group when neither of the combinations forms a ring; Z is a phenyl group which may have 1, 2 or 3 substituents selected from halogen atoms; A is a hydrogen atom, a $C_1$–$C_4$ lower alkyl group or a $C_1$–$C_4$ lower alkoxy group; and G is a benzoyl group which may have 1, 2 or 3 substituents selected from halogen atoms and lower alkoxy groups.

(6) A compound or a pharmacologically acceptable salt thereof according to the above item 1, wherein $R^1$ and $R^2$ are taken together to form a $C_2$–$C_5$ alkylene group or a $C_2$–$C_5$ alkenylene group; $R^3$ is a hydrogen atom, a lower alkyl group, an aryl group, a lower alkoxycarbonyl group, a hydroxyl-lower-alkyl group, an amino protecting groups represented by $NR_aCOR_b$ wherein $R_a$ and $R_b$ are as defined above, or an amino protecting groups represented by $NR_a$-$COOR_b$ wherein $R_a$ and $R_b$ are as defined above; Z is a phenyl group which may have 1, 2 or 3 substituents selected from halogen atoms; A is a hydrogen atom, a $C_1$–$C_4$ lower alkyl group or a $C_1$–$C_4$ lower alkoxy group; and G is a benzoyl group which may have 1, 2 or 3 substituents selected from halogen atoms and lower alkoxy groups.

(7) A compound or a pharmacologically acceptable salt thereof according to the above item 1, which is selected from the following compounds:

2-[(±)-4-(N-benzoyl-N-methyl)amino-3-(3,4-dichlorophenyl)butyl]-1,2,3,4,6,7,8,9-octahydro-benzo[b][1,6]naphthyridine or a pharmacologically acceptable salt thereof, 2-[(±)-4-(N-benzoyl-N-methyl)amino-3-(3,4-dichlorophenyl)butyl]-1,2,3,4-tetrahydro-benzo[b][1,6]-naphthyridine-10-carboxamide or a pharmacologically acceptable salt thereof, 2-[(±)-4-(N-benzoyl-N-methyl)amino-3-(3,4-dichlorophenyl)butyl]-10-methoxycarbonyl-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-1,2,3,4-tetrahydro-benzo[b][1,6]-naphthyridine-10-carboxylic acid or a pharmacologically acceptable salt thereof, 10-amino-2-[(±)-4-(N-benzoyl-N-methyl) amino-3-(3,4-dichlorophenyl)butyl]-1,2,3,4-tetrahydro-benzo[b][1,6]naphthyridine or a pharmacologically acceptable salt thereof, 2-[(±)-4-(N-benzoyl-N-methyl) amino-3-(3,4-dichlorophenyl)butyl]-10-hydroxymethyl- 1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-10-acetylamino-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-10-phenyl-1,2,3,4-tetrahydro-benzo[b][1,6]naphthyridine or a pharmacologically acceptable salt thereof, 2-[ (±)-4-(N-benzoyl-N-methyl)amino-3-(3,4-dichlorophenyl)butyl]-10-methoxycarbonylamino-1,2,3,4-tetrahydro-benzo[b][1,6]naphthyridine or a pharmacologi- cally acceptable salt thereof, 2-[(±)-4-(N-benzoyl-N-methyl)amino-3-(3,4-dichlorophenyl)butyl]-10-(N-methyl-N-methoxycarbonyl)-amino-1,2,3,4-tetrahydro-benzo[b][1,6]naphthyridine or a pharmacologically acceptable salt thereof, 2-[ (±)-4-(N-benzoyl-N-methyl)amino-3-(3,4-dichlorophenyl)butyl]-10-chloro-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-10-benzoylamino-1,2,3,4-tetrahydro- benzo[b][1,6]naphthyridine or a pharmacologically acceptable salt thereof, 2[-(±)-4-(N-benzoyl-N-methyl)amino-3-(3,4-dichlorophenyl)butyl]-10-acetylamino-1,2,3,4,6,7,8,9-octahydro-benzo[b][1,6]naphthyridine or a pharmacologically acceptable salt thereof, 2-[(±)-4-(N-benzoyl-N-methyl)amino-3-(3,4-difluorophenyl)butyl]-1,2,3,4,6,7,8,9-octahydro-benzo[b][1,6]naphthyridine or a pharmacologically acceptable salt thereof, and 2-[(±)-4-(N-benzoyl-N-methyl)amino-3-(3,4-difluorophenyl)butyl]-10-acetylamino-1,2,3,4-tetrahydro-benzo[b][1,6]naphthyridine or a pharmacologically acceptable salt thereof.

(8) A compound or a pharmacologically acceptable salt thereof according to the above item 1, which is selected from the following compounds:

2-[(−)-4-(N-benzoyl-N-methyl)amino-3-(3,4-dichlorophenyl)butyl]-1,2,3,4,6,7,8,9-octahydro-benzo[b][1,6]naphthyridine or a pharmacologically acceptable salt thereof, 2-[(−)-4-(N-benzoyl-N-methyl)amino-3-(3,4-dichlorophenyl)butyl]-1,2,3,4-tetrahydro-benzo[b][1,6]-naphthyridine-10-carboxamide or a pharmacologically acceptable salt thereof, methyl 2-[(−)-4-(N-benzoyl-N-methyl)amino-3-(3,4-dichlorophenyl)butyl]-10-methoxycarbonyl-1,2,3,4-tetrahydro-benzo[b][1,6]naphthyridine-10-carboxylate or a pharmacologically acceptable salt thereof, 2-[(−)-4-(N-benzoyl-N-methyl)amino-3-(3,4-dichlorophenyl)butyl]-1,2,3,4-tetrahydro-benzo[b][1,6]-naphthyridine-10-carboxylic acid or a pharmacologically acceptable salt thereof, 10-amino-2-[(−)-4-(N-benzoyl-N-methyl)amino-3-(3,4-dichlorophenyl)butyl]-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-hydroxymethyl-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-acetylamino-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-phenyl-1,2,3,4-tetrahydrobenzo[b][1,6]naphthyridine or a pharmacologically acceptable salt thereof, 2-[(-)-4-(N-benzoyl-N-methyl)amino-3-(3,4-dichlorophenyl)butyl]-10-methoxycarbonylamino-1,2,3,4-tetrahydro-benzo[b][1,6]naphthyridine or a pharmacologically acceptable salt thereof, 2-[(-)-4-(N-benzoyl-N-methyl)amino-3-(3,4-dichlorophenyl)butyl]-10-(N-methyl-N-methoxycarbonyl)-amino-1,2,3,4-tetrahydro-benzo[b][1,6]naphthyridine or a pharmacologically acceptable salt thereof, 2-[(-)-4-(N-benzoyl-N-methyl)amino-3-(3,4-dichlorophenyl)butyl]-10-chloro-1,2,3,4-tetrahydro-benzo[b][1,6]naphthyridine or a pharmacologically acceptable salt thereof, 2-[(-)-4-(N-benzoyl-N-methyl)amino-3-(3,4-dichlorophenyl)butyl]-10-benzoylamino-1,2,3,4-tetrahydro- benzo[b][1,6]naphthyridine or a pharmacologically acceptable salt thereof, 2-[(-)-4-(N-benzoyl-N-methyl)amino-3-(3,4-dichlorophenyl)butyl]-10-acetylamino-1,2,3,4,6,7,8,9-octahydro-benzo[b][1,6]naphthyridine or a pharmacologically acceptable salt thereof, 2-[(-)-4-(N-benzoyl-N-methyl)amino-3-(3,4-difluorophenyl)butyl]-1,2,3,4,6,7,8,9-octahydro-benzo[b][1,6]naphthyridine or a pharmacologically acceptable salt thereof, and 2-[(-)-4-(N-benzoyl-N-methyl)amino-3-(3,4-difluorophenyl)butyl]-10-acetylamino-1,2,3,4-tetrahydro-benzo[b][1,6]naphthyridine or a pharmacologically acceptable salt thereof.

(9) A process for producing a compound according to any one of the above items 1 to 8, which comprises carrying out reductive alkylation by using a 5,6,7,8-tetrahydro-1,6-naphthyridine represented by the following general formula (2):

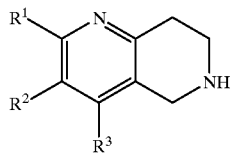

(2)

wherein $R^1$, $R^2$ and $R^3$ are as defined above, and an aldehyde represented by the following general formula (3):

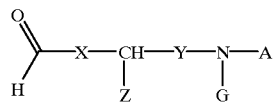

(3)

wherein X, Y, Z, A and G are as defined above.

(10) A process for producing a compound according to any one of the above items 1 to 8, which comprises N-alkylating a compound represented by the following general formula (2):

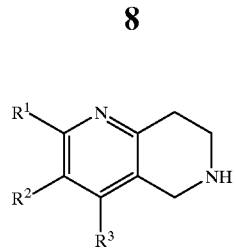

(2)

wherein $R^1$, $R^2$ and $R^3$ are as defined above, with a compound represented by the following general formula (4):

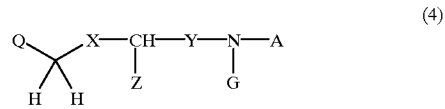

(4)

wherein X, Y, Z, A and G are as defined above, Q is a halogen atom or a $R_4SO_2O$— group wherein $R_4$ is a lower alkyl group, an aryl group, a trifluoromethyl group or the like.

(11) A pharmaceutical composition comprising a compound or a pharmacologically acceptable salt thereof according to any one of the above items 1 to 8, and a pharmaceutically acceptable diluent or carrier.

(12) A compound represented by the following general formula (5):

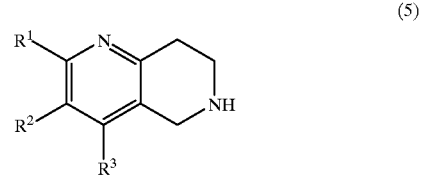

(5)

wherein $R^1$, $R^2$ and $R^3$ are as defined above, except
    ethyl 2-chloro-5,6,7,8-tetrahydro-1,6-naphthyridine-3-carboxylate,
    5,6,7,8-tetrahydro-9-methyl-thieno[3,2-b][1,6]-naphthyridine,
    1,2,3,4-tetrahydro-10-phenyl-benzo[b][1,6]-naphthyridine,
    6,7,8,9-tetrahydro-5-phenyl-pyrido[2,3-b][1,6]-naphthyridine,
    8-chloro-1,2,3,4-tetrahydro-N-methyl-benzo[b][1,6]naphthyridine-10-amine,
    1,2,3,4-tetrahydro-benzo[b][1,6]naphthyridine-10-amine,
    5,6,7,8-tetrahydro-3-methyl-1,6-naphthyridine,
    6,7,8,9-tetrahydro-5-methyl-pyrido[2,3-b][1,6]-naphthyridine,
    8-fluoro-1,2,3,4-tetrahydro-benzo[b][1,6]-naphthyridine-10-amine,
    5,6,7,8-tetrahydro-1,6-naphthyridine,
    1,2,3,4-tetrahydro-10-methyl-benzo[b][1,6]-naphthyridine,
    2,3,5,6,7,8-hexahydro-9-methyl-thieno[3,2-b][1,6]naphthyridine,
    1,2,3,4-tetrahydro-8-methoxy-N-methyl-benzo[b][1,6]naphthyridine-10-amine,
    ethyl 5,6,7,8-tetrahydro-4-hydroxy-1,6-naphthyridine-3-carboxylate,
    1,2,3,4-tetrahydro-N-methyl-benzo[b][1,6]-naphthyridine-10-amine, 2,3,4,6,7,8-hexahydro-1H-cyclopenta[b][1,6]-naphthyridine, 8-chloro-1,2,3,4-tetrahydro-benzo[b][1,6]-naphthyridine-10-amine, 5,6,7,8-tetrahydro-3-nitro-1,6-naphthyridine, 5,6,7,8-tetrahydro-9-phenyl-thiazolo[4,5-b][1,6]naphthyridine, 8-chloro-1,2,3,4-tetrahydro-10-phenyl-benzo[b][1,6]naphthyridine, 5,6,7,8-tetrahydro-2,3-dimethyl-4-phenyl-thieno[2,3-b][1,6]naphthyridine, 8-fluoro-1,2,3,4-tetrahydro-N-methyl-benzo[b][1,6]naphthyridine-10-amine, 1,2,3,4,6,7,8,9-octahydro-benzo[b][1,6]-naphthyridine, 6,7,8,9-tetrahydro-5-methylpyrido[2,3-b][1,6]-naphthyridine, 1,2,3,4-tetrahydro-8-methoxy-benzo[b][1,6]-naphthyridine-10-amine, and 5,6,7,8-tetrahydro-2-methyl-1,6-naphthyridine.

Compounds of the general formula (2) are useful as an intermediate for producing the compound of the present invention represented by the general formula (1).

(13) An antagonist at tachykinin receptors, comprising a compound or a pharmacologically acceptable salt thereof according to any one of the above items 1 to 8 as an active ingredient.

(14) An antagonist at NK-2 receptors, comprising a compound or a pharmacologically acceptable salt thereof according to any one of the above items 1 to 8 as an active ingredient.

(15) A pharmaceutical composition for the prophylaxis or treatment of bronchitis, pollakiuria, urinary incontinence and colitis, comprising a compound or a pharmacologically acceptable salt thereof according to any one of the above items 1 to 8 as an active ingredient.

(16) A pharmaceutical composition for the prophylaxis or treatment of asthma comprising a compound or a pharmacologically acceptable salt thereof according to any one of the above items 1 to 8 as an active ingredient.

(17) A compound or a pharmacologically acceptable salt thereof according to any one of the above items 1 to 8, for use as an active ingredient of a pharmaceutical composition.

(18) Use of a compound or a pharmacologically acceptable salt thereof according to any one of the above items 1 to 8 in the manufacture of an antagonist at tachykinin receptors comprising said compound or salt thereof as an active ingredient.

(19) A method for preventing or treating diseases in which tachykinin receptors participate, which comprises administering to a patient a compound or a pharmacologically acceptable salt thereof according to any one of the above items 1 to 8.

The compounds of the present invention show an excellent antagonism against tachykinins and are useful as prophylactic or therapeutic agents for the following tachykinin-mediated diseases of mammals such as mouse, rat, hamster, rabbit, cat, dog, cattle, sheep, monkey, man, etc.: respiratory diseases such as asthma, bronchitis, pneumonia, chronic obstructive pulmonary disease, bronchoconstriction, expectoration, cough, etc.; urinary diseases such as pollakiuria, urinary incontinence, cystitis, prostatitis, etc.; central diseases such as anxiety, insomnia, depression, manic-depressive psychosis, temper, Parkinson's disease, psychosomatic disorder, mental diseases, schizophrenia, etc.; neurodegenerative diseases such as dementia in the case of AIDS, Alzheimer type senile dementia, Alzheimer's disease, Down's syndrome, Huntingon's chorea, etc.; demyelinating diseases such as amyotrophic lateral sclerosis, etc.; other neuropathies such as neurophathies due to diabetes, AIDS, chemotherapy or the like and other peripheral neuropathies; neuralgia; digestive organ diseases such as diseases due to a disorder of visceral nerve, irritable bowel syndrome, ulcerative colitis, Crohn's disease, etc.; vomitting such as vomitting induced by X-ray irradiation, chemotherapeutic drugs, poisonous substances, toxins, pregnancy, vestibular dysfunction, postoperative diseases, obstruction of stomach and intestines, decrease in gastrointestinal motility, visceral pain, migraine, intracranical pressure increase, intracranical pressure disease, or adverse side effects of administration of various drugs; collagen disease; scleroderma; eosinophilia due to infection of distomatosis; circulatory diseases such as angina pectori, hypertension, heart failure, thrombosis, migraine, and Raynaud's disease; pains such as nociperception, e.g., pains associated with, for example, cancer, angina, and acute and chronic inflammations, and pains of neuralgia and migraine; allergic diseases such as allergic rhinitis, urticaria, other eczematoid dermatitis and contact dermatitis; hypersensitivity diseases such as hypersensitivity diseases to plants; ophthalmic diseases such as conjunctivitis, spring catarrh, the destruction of blood-aqueous barrier caused by various inflammatory eye diseases, an increase of intraocular pressure, miosis, etc.; inflammatory diseases such as colitis, psoriasis, fibrositis, rheumatoid arthritis, osteoarthritis, nephritis, hepatitis, etc.; osteoporosis; addiction such as alcohol dependence; somatic diseases due to stress; reflex sympathetic dystrophy such as shoulder-hand syndrome; dysthymia; undesirable immunoreactions such as graft rejection and immunoactivation; and diseases associated with immunodepression, such as systemic lupus erythematosus and multiple sclerosis. Furthermore, the compounds of the present invention are useful in all cases where antagonism against tachykinins is desired.

BEST MODE FOR CARRYING OUT THE INVENTION

In the present invention, as the lower alkyl group, there may be exemplified linear or branched alkyl groups of 1 to 4 carbon atoms, such as methyl group, ethyl group, n-propyl group, isopropyl group, n-butyl group, sec-butyl group, tert-butyl group, etc. Of these, methyl group and ethyl group may be exemplified as preferable groups.

The cycloalkyl group refers to a saturated cyclic group of 3 to 8 carbon atoms, and preferable examples thereof are cyclopentyl group and cyclohexyl group.

In the present invention, the lower alkoxy group refers to a linear or branched alkoxy group of 1 to 4 carbon atoms and includes, for example, methoxy group, ethoxy group, n-propoxy group, isopropoxy group, n-butoxy group, isobutoxy group and tert-butoxy group. Of these, methoxy group and ethoxy group may be exemplified as preferable groups.

In the present invention, the halogen atom includes fluorine atom, chlorine atom, bromine atom and iodine atom.

In the present invention, the aryl group refers to an aryl group of 6 to 14 carbon atoms and includes, for example, phenyl group, biphenyl group, naphthyl group, anthryl group and phenanthryl group. Of these, phenyl group and naphthyl group may be exemplified as preferable groups.

In the present invention, the heteroaryl group refers to an unsaturated 5- to 7-membered ring containing 1 to 5 (preferably 1 or 2) heteroatoms preferably selected from nitrogen atom, oxygen atom and sulfur atom. Specific examples thereof are thienyl, imidazolyl, pyridinyl, pyrimidinyl, pyridazinyl, etc.

As the lower acyl group, there may be exemplified lower acyl groups of 1 to 6 carbon atoms, such as formyl group, acetyl group, propanoyl group, butanoyl group, pentanoyl group, hexanoyl group, etc.

As the alkenyl group, there may be exemplified alkenyl groups of 2 to 6 carbon atoms, such as ethynyl group, propenyl group, butynyl group, pentenyl group, hexenyl group, etc.

The $C_2$–$C_5$ alkylene group includes ethylene group, propylene group, butylene group, pentylene group, hexylene group, etc.

The $C_2$–$C_5$ alkenylene group includes ethynylene group, propenylene group, butynylene group, pentenylene group, hexenylene group, etc.

The compound of the general formula (1) exists as a single optically active substance or a racemic modification since it has an asymmetric carbon atom. Such a compound may be isolated as the optically active substance or the racemic modification. It should be understood that the present invention includes all of such racemic modifications, optically active substances, or mixtures thereof, which are antagonistic to NK-2.

The pharmacologically acceptable salt of the heterocyclic compound of the present invention includes, for example, salts with mineral acids such as hydrochloric acid, sulfuric acid, etc.; and salts with organic acids such as acetic acid, lactic acid, succinic acid, fumaric acid, maleic acid, citric acid, benzoic acid, methanesulfonic acid, p-toluenesulfonic acid, etc. These salts may be produced by conventional processes.

The compound represented by the general formula (1) includes, for example, the following compounds:

(1) 2-[(±)-4-(N-benzoyl-N-methyl)amino-3-(3,4-dichlorophenyl)butyl]-1,2,3,4,6,7,8,9-octahydro-benzo[b][1,6]naphthyridine or a salt thereof, (2) 2-{2-[N-(2-naphthoyl)aminoethyl]}-1,2,3,4,6,7,8,9-octahydro-benzo[b][1,6]naphthyridine or a salt thereof, (3) 2-{2-{N-[4-(2-phenyl)quinolinecarbonyl]}-aminoethyl}-1,2,3,4,6,7,8,9-octahydro-benzo[b][1,6]-naphthyridine or a salt thereof, (4) 2-{3-[N-(1-naphthoyl)aminopropyl]}-1,2,3,4,6,7,8,9-octahydro-benzo[b][1,6]naphthyridine or a salt thereof, (5) 2-[(−)-4-(N-benzoyl-N-methyl)amino-3-(3,4-dichlorophenyl)butyl]-1,2,3,4-tetrahydro-benzo[b][1,6]-naphthyridine-10-carboxamide or a pharmacologically acceptable salt thereof, (6) 2-[(−)-4-(N-benzoyl-N-methyl)amino-3-(3,4-dichlorophenyl)butyl]-10-methoxycarbonyl-1,2,3,4-tetrahydro-benzo[b][1,6]naphthyridine or a pharmacologically acceptable salt thereof, (7) 2-[(−)-4-(N-benzoyl-N-methyl)amino-3-(3,4-dichlorophenyl)butyl]-1,2,3,4-tetrahydro-benzo[b][1,6]-naphthyridine-10-carboxylic acid or a pharmacologically acceptable salt thereof, (8) 10-amino-2-[(−)-4-(N-benzoyl-N-methyl)-amino-3-(3,4-dichlorophenyl)butyl]-1,2,3,4-tetrahydro-benzo[b][1,6]naphthyridine or a pharmacologically acceptable salt thereof, (9) 2-[(−)-4-(N-benzoyl-N-methyl)amino-3-(3,4-dichlorophenyl)butyl]-10-hydroxymethyl-1,2,3,4-tetrahydro-benzo[b][1,6]naphthyridine or a pharmacologically acceptable salt thereof,

(10) 2-[(−)-4-(N-benzoyl-N-methyl)amino-3-(3,4-dichlorophenyl)butyl]-10-acetylamino-1,2,3,4-tetrahydro-benzo[b][1,6]naphthyridine or a pharmacologically acceptable salt thereof,

(11) 2-[(−)-4-(N-benzoyl-N-methyl)amino-3-(3,4-dichlorophenyl)butyl]-10-phenyl-1,2,3,4-tetrahydro-benzo[b][1,6]naphthyridine or a pharmacologically acceptable salt thereof,

(12) 2-[(−)-4-(N-benzoyl-N-methyl)amino-3-(3,4-dichlorophenyl)butyl]-10-methoxycarbonylamino-1,2,3,4-tetrahydro-benzo[b][1,6]naphthyridine or a pharmacologically acceptable salt thereof,

(13) 2-[(−)-4-(N-benzoyl-N-methyl)amino-3-(3,4-dichlorophenyl)butyl]-10-(N-methyl-N-methoxycarbonyl)amino-1,2,3,4-tetrahydro-benzo[b][1,6]-naphthyridine or a pharmacologically acceptable salt thereof,

(14) 2-[(−)-4-(N-benzoyl-N-methyl)amino-3-(3,4-dichlorophenyl)butyl]-10-chloro-1,2,3,4-tetrahydro-benzo[b][1,6]naphthyridine or a pharmacologically acceptable salt thereof,

(15) 2-[(−)-4-(N-benzoyl-N-methyl)amino-3-(3,4-dichlorophenyl)butyl]-10-benzoylamino-1,2,3,4-tetrahydro-benzo[b][1,6]naphthyridine or a pharmacologically acceptable salt thereof,

(16) 2-[(−)-4-(N-benzoyl-N-methyl)amino-3-(3,4-dichlorophenyl)butyl]-10-acetylamino-1,2,3,4,6,7,8,9-octahydro-benzo[b][1,6]naphthyridine or a pharmacologically acceptable salt thereof,

(17) 2-[(−)-4-(N-benzoyl-N-methyl)amino-3-(3,4-difluorophenyl)butyl]-1,2,3,4,6,7,8,9-octahydro-benzo[b][1,6]naphthyridine or a pharmacologically acceptable salt thereof, and

(18) 2-[(−)-4-(N-benzoyl-N-methyl)amino-3-(3,4-difluorophenyl)butyl]-10-acetylamino-1,2,3,4-tetrahydro-benzo[b][1,6]naphthyridine or a pharmacologically acceptable salt thereof.

Next, a process for producing the compound of the present invention is explained below. In each chemical formula, $R^1$, $R^2$, $R^3$, X, Y, Z, A and G are as defined above.

The naphthyridine derivative of the general formula (1) may be produced by carrying out reductive amination by using a compound of the general formula (2) and a suitable aldehyde of the general formula (3).

The reductive amination may be carried out at −20° C. to reflux temperature in a solvent such as a lower alcohol (e.g. methanol or ethanol), an ether (e.g. tetrahydrofuran) or dichloromethane by the use of a reducing agent such as sodium cyanotrihydroborate or sodium tetrahydroborate in the presence or absence of a Lewis acid such as titanium(IV) isopropoxide, titanium(IV) chloride or boron trifluoride diethyl ether complex; an acid such as acetic acid or hydrochloric acid; or a dehydrating agent such as molecular sieve.

The reaction may be carried out at 0° C. to 100° C. under a hydrogen atmosphere in a solvent such as an alcohol (e.g. methanol or ethanol), ethyl acetate or acetic acid by the use of a reduction catalyst (e.g. palladium-carbon or Raney nickel) in the presence or absence of acetic acid, hydrochloric acid or the like.

As an alternative process, the compound of the general formula (1) may be obtained also by N-alkylating a compound of the general formula (2) at its nitrogen atom in the ring with a compound of the general formula (4).

In the general formula (4), Q is a removable group generally used in N-alkylation, such as a halogen atom or a $R_4SO_2O$- group wherein $R_4$ is a lower alkyl group, an aryl group, an aralkyl group or the like. The above N-alkylation may be carried out in a solvent such as dimethylformamide or 2-butanone or without any solvent in the presence or absence of a base such as potassium carbonate or triethylamine. The N-alkylation may be carried out at 0° C. to reflux temperature.

The compound of the general formula (2) is useful as an intermediate. Some compounds of the general formula (2) are well known. More specifically, the following compounds are well known:

ethyl 2-chloro-5,6,7,8-tetrahydro-1,6-naphthyridine-3-carboxylate hydrochloride,
5,6,7,8-tetrahydro-9-methyl-thieno[3,2-b][1,6]naphthyridine dihydrochloride,
1,2,3,4-tetrahydro-10-phenyl-benzo[b][1,6]-naphthyridine dihydrochloride,
6,7,8,9-tetrahydro-5-phenyl-pyrido[2,3-b][1,6]naphthyridine dihydrochloride,
8-chloro-1,2,3,4-tetrahydro-N-methyl-benzo[b][1,6) naphthyridine-10-amine,
1,2,3,4-tetrahydro-benzo[b][1,6]naphthyridine-10-amine,
5,6,7,8-tetrahydro-3-methyl-1,6-naphthyridine,
6,7,8,9-tetrahydro-5-methyl-pyrido[2,3-b][1,6]naphthyridine,
8-fluoro-1,2,3,4-tetrahydro-benzo[b][1,6]-naphthyridine-10-amine,
5,6,7,8-tetrahydro-1,6-naphthyridine,
1,2,3,4-tetrahydro-10-methyl-benzo[b][1,6]-naphthyridine dihydrochloride,
2,3,5,6,7,8-hexahydro-9-methyl-thieno[3,2-b][1,6]naphthyridine dihydrochloride,
1,2,3,4-tetrahydro-8-methoxy-N-methyl-benzo[b][1,6]naphthyridine-10-amine,
ethyl 5,6,7,8-tetrahydro-4-hydroxy-1,6-naphthyridine-3-carboxylate,
6,7,8,9-tetrahydro-5-phenyl-pyrido[2,3-b][1,6]naphthyridine,
1,2,3,4-tetrahydro-N-methyl-benzo[b][1,6]-naphthyridine-10-amine,
5,6,7,8-tetrahydro-1,6-naphthyridine hydrochloride,
2,3,4,6,7,8-hexahydro-1H-cyclopenta[b][1,6]-naphthyridine,
5,6,7,8-tetrahydro-3-methyl-1,6-naphthyridine dihydrochloride, 8-chloro-1,2,3,4-tetrahydro-benzo[b][1,6]-naphthyridine-10-amine,
5,6,7,8-tetrahydro-3-nitro-1,6-naphthyridine,
5,6,7,8-tetrahydro-9-phenyl-thiazolo[4,5-b][1,6]naphthyridine,
8-chloro-1,2,3,4-tetrahydro-10-phenyl-benzo[b][1,6]naphthyridine,
5,6,7,8-tetrahydro-2,3-dimethyl-4-phenyl-thieno[2,3-b][1,6]naphthyridine,
8-fluoro-1,2,3,4-tetrahydro-N-methyl-benzo[b][1,6]naphthyridine-10-amine,
1,2,3,4,6,7,8,9-octahydro-benzo[b][1,6]-naphthyridine,
6,7,8,9-tetrahydro-5-methylpyrido[2,3-b][1,6]-naphthyridine dihydrochloride,
1,2,3,4-tetrahydro-8-methoxy-benzo[b][1,6]-naphthyridine-10-amine,
5,6,7,8-tetrahydro-2-methyl-1,6-naphthyridine, and
1,2,3,4-tetrahydro-10-phenyl-benzo[b][1,6]-naphthyridine.

Compounds of the general formula (2) except the well-known compounds are novel and are represented by the general formula (5). The well-known compounds may be produced, for example, by the processes disclosed in Japanese Patent Unexamined Publication No. 58-57379, J. Heterocyclic Chem., 33, 1807 (1996), Japanese Patent Unexamined Publication No. 3-2166, J. Chem. Soc., 708 (1964), J. Org. Chem., 2899 (1966), and J. Med. Chem., 32, 1295 (1989). The novel compounds of the general formula (5) may be individually prepared by the following per se well-known process (a), (b), (c), (d), (e), (f), (g), (h) or (i).

Production Process (a)

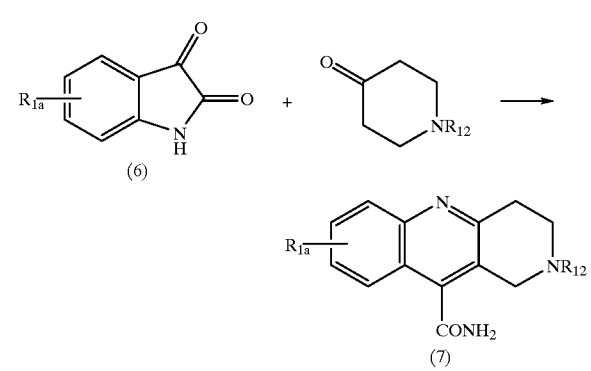

wherein $R_{1a}$ is a hydrogen atom, a halogen atom or a nitro group, and $R_{12}$ is an amino-protecting group (e.g. a tert-butoxycarbonyl group, a benzyloxycarbonyl group, a 9-fluorenylmethyloxycarbonyl group, an acetyl group, a formyl group or a benzyl group).

In detail, a compound of the general formula (7) may be obtained by reacting a compound of the general formula (6) with an N-protected piperidone at 100–130° C. on an oil bath in a solvent such as dimethylformamide in the presence of ammonium acetate or the like.

Production Process (b)

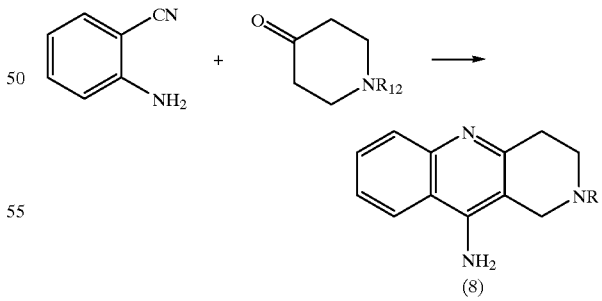

wherein $R_{12}$ is as defined above. In detail, a compound of the general formula (8) may be obtained by reacting anthranilonitrile with an N-protected piperidone at 90° C. to reflux temperature without any solvent or in a solvent such as dimethylformamide or dimethylacetamide in the presence of zinc chloride of the like.

Production Process (c)

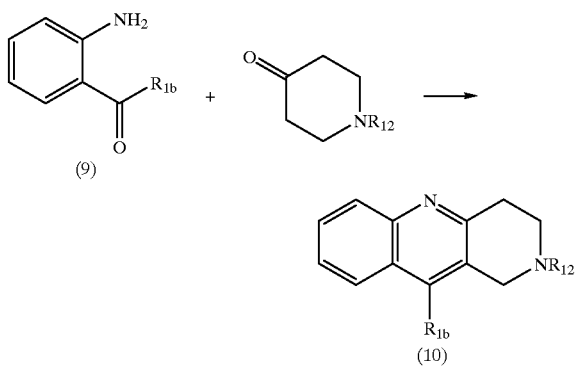

wherein $R_{1b}$ is a lower alkyl group or an aryl group, and $R_{12}$ is as defined above. In detail, a compound of the general formula (10) may be obtained by reacting a compound of the general formula (9) with an N-protected piperidone at 130–160° C. on an oil bath without any solvent or in a solvent such as an alcohol (e.g. methanol or ethanol) or dimethylformamide in the presence of an acid such as sulfuric acid, acetic acid or hydrochloric acid; a base such as potassium hydroxide or sodium hydroxide; a salt such as ammonium acetate or piperidine acetate; or a Lewis acid such as anhydrous ammonium chloride or titanium tetrachloride.

Production Process (d)

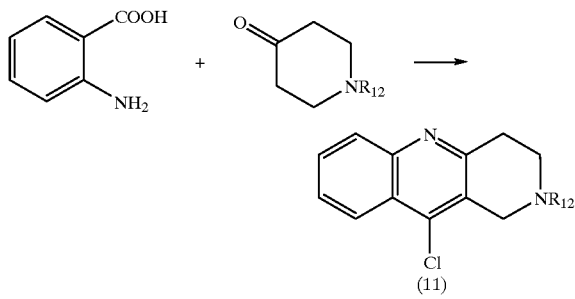

wherein $R_{12}$ is as defined above. In detail, a compound of the general formula (11) may be obtained by adding phosphorus oxychloride to anthranilic acid and an N-protected piperidone and carrying out the reaction with heating under reflux.

Production Process (e)

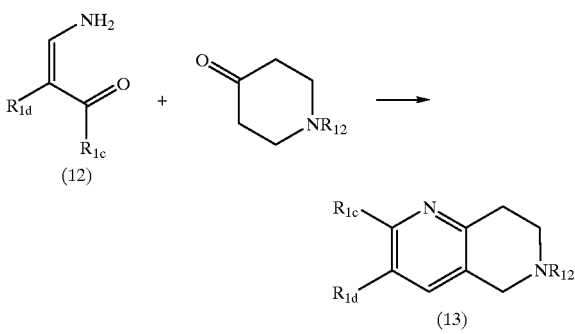

wherein each of $R_{1c}$ and $R_{1d}$ is a hydrogen atom or a lower alkyl group, and $R_{12}$ is as defined above. In detail, a compound of the general formula (13) may be obtained by reacting a compound of the general formula (12) with an N-protected piperidone at 130–160° C. on an oil bath without any solvent or in a solvent such as an alcohol (e.g. methanol or ethanol) or dimethylformamide in the presence of an acid such as sulfuric acid, acetic acid or hydrochloric acid; a base such as potassium hydroxide or sodium hydroxide; a salt such as ammonium acetate or piperidine acetate; or a Lewis acid such as anhydrous ammonium chloride or titanium tetrachloride.

Production Process (f)

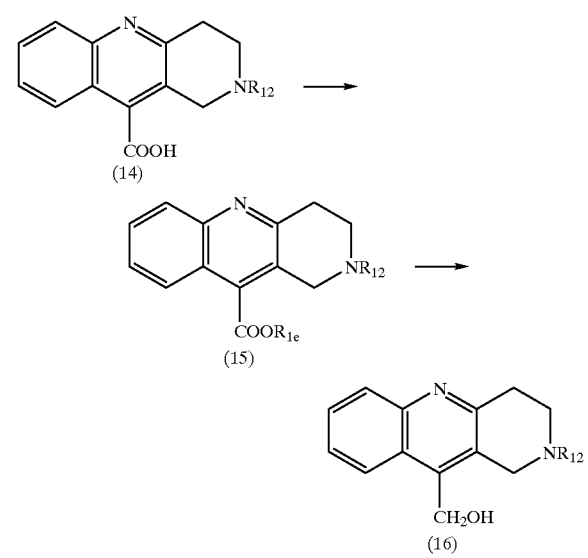

wherein $R_{1e}$ is a lower alkyl group, and $R_{12}$ is as defined above. In detail, a compound of the general formula (15) may be obtained by reacting a compound of the general formula (14) with a lower halogenoalkyl group at room temperature to reflux temperature in a solvent such as an alcohol (e.g. methanol or ethanol), acetone or dimethylformamide in the presence of a base catalyst such as potassium carbonate, potassium hydroxide or sodium hydroxide or in the presence of an acid catalyst such as sulfuric acid or hydrochloric acid.

A compound of the general formula (16) may be obtained by reducing the compound of the general formula (15). This reaction may be carried out at −78° C. to reflux temperature, for example, by using a reducing agent such as lithium tetrahydroborate, calcium tetrahydroborate or aluminum lithium hydride and a solvent such as water or an organic solvent such as an alcohol (e.g. methanol or ethanol), an ether (e.g. tetrahydrofuran, dimethyl ether or dioxane) or toluene.

Production Process (g)

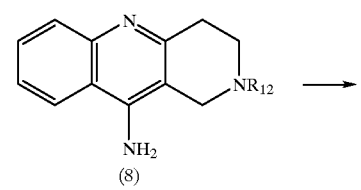

-continued

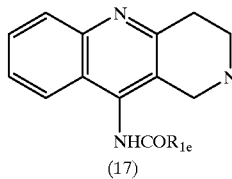

(17)

wherein $R_{1e}$ is as defined above. In detail, a compound of the general formula (17) may be obtained by reacting a compound of the general formula (8) with an acid halide or an acid anhydride. The acid halide includes acetyl chloride, acetyl bromide, butyryl chloride, etc. The acid anhydride includes acetic anhydride, trifluoroacetic anhydride, etc. The reaction may be carried out at −20° C. to reflux temperature. A satisfactory result can be obtained when the reaction is carried out in the presence of a base catalyst. The base catalyst includes sodium hydroxide, pyridine, triethylamine, 4-dimethyl-aminopyridine, etc. As to a solvent for the reaction, no solvent is used, or there is used water or an organic solvent such as an ether (e.g. tetrahydrofuran, dimethyl ether or dioxane), or a halogen-containing solvent such as methylene chloride or chloroform.

Production Process (h)

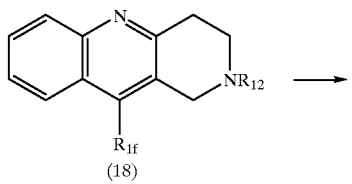

(18)

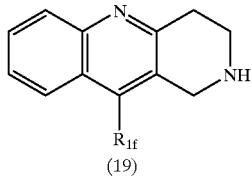

(19)

wherein $R_{1f}$ is a hydrogen atom, an aminocarbonyl group represented by $CONR_aR_b$ wherein $R_a$ and $R_b$ are as defined above, an amino group, a lower alkyl group, an aryl group, a halogen atom, a lower alkoxycarbonyl group, a carboxyl group, a hydroxyl-lower-alkyl group, an amino protector represented by $NR_aCOR_b$ wherein $R_a$ and $R_b$ are as defined above, or an amino protector represented by $NR_aCOOR_b$ wherein $R_a$ and $R_b$ are as defined above, and $R_{12}$ is as defined above.

In detail, a compound of the general formula (19) may be obtained by subjecting a compound of the general formula (18) to deprotection by a conventional method such as acid or alkali hydrolysis, catalytic reduction or the like.

When the protecting group is a benzyl group, the deprotection may be carried out under a hydrogen atmosphere at room temperature to 50° C. by the use of a reduction catalyst (e.g. palladium-carbon, palladium black, palladium hydroxide-carbon or Raney nickel) in methanol, ethanol, water, acetic acid, trifluoroacetic acid or the like. The deprotection may be carried out also by reacting a compound of the general formula (18) by the use of chloroformic acid-(chloroethyl) at 0° C. to reflux temperature in a solvent (e.g. dichloromethane or tetrahydrofuran), and then heating the residue under reflux in an alcohol solvent (e.g. methanol or ethanol).

Production Process (i)

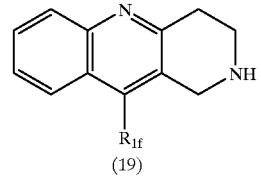

(19)

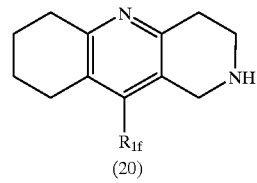

(20)

wherein $R_{1f}$ is as defined above. In detail, a compound of the general formula (20) may be obtained by reacting a compound of the general formula (19) under a hydrogen atmosphere at room temperature to 50° C. by the use of platinum oxide or the like in trifluoroacetic acid.

For purifying the product by isolation from the reaction mixture obtained by adopting each of the above production processes, solvent extraction, concentration, recrystallization, chromatography, etc. each by a conventional method are properly employed.

A salt of the compound of the present invention can easily be produced by a conventional salt-forming reaction.

When the compound of the present invention is used as an antagonist for tachykinin receptor, it is orally or parenterally administered after being formulated alone or in admixture with an excipient or a carrier into a pharmaceutical composition such as a suspension, an emulsion, an injection, an inhallation, tablets, pills, granules, fine subtilaes, a powder, capsules, an oral solution, a suppository, an ophthalmic solution, an ophthalmic ointment, a percutaneous solution, a percutaneous patch, an ointment, a trans-mucosal solution, a trans-mucosal patch, a spray or the like. As the additive such as the excipient or the carrier, a pharmaceutically acceptable one is chosen, and its kind and proportion depend on administration route and administration method. For example, in the case of the injection, sodium chloride and sugars such as glucose and mannitol are usually preferable. In the case of the compositions for oral administration, starch, lactose, crystalline cellulose, magnesium stearate, etc. are preferable. If desired, the above-exemplified pharmaceutical compositions may contain assistants, stabilizers, wetting agents, emulsifiers, buffers and other conventional additives.

Although the content of the compound of the present invention in the pharmaceutical composition is varied depending on the kind of the composition, it is usually 0.1 to 100% by weight, preferably 1 to 98% by weight. For example, the injection contains the active ingredient in an amount of usually 0.1 to 30% by weight, preferably 1 to 10% by weight. In the case of the compositions for oral administration, the compound of the present invention is used together with additives in the form of tablets, capsules, a powder, granules, a solution, a dry syrup or the like. The capsules, tablets, granules or powder usually contains the active ingredient in an amount of 5 to 100% by weight, preferably 25 to 98% by weight.

The dose is determined depending on, for example, the age, sex, body weight and symptom of a patient and purpose of treatment. For treatment, the compound of the present invention is usually administered in a dose of 0.001 to 100 mg/kg/day in the case of parenteral administration, or 0.01 to 500 mg/kg/day, preferably 0.1 to 100 mg/kg/day, in the case of oral administration, in one portion or 2 to 4 portions.

The present invention is illustrated by describing non-limitative examples below. The following procedure was employed unless otherwise specified.

The present invention is illustrated with the following examples. Since starting compounds used for producing compounds of the present invention (1) include novel compounds, examples of the production of such starting compounds are also explained as working examples. Each of compounds needed in the production process of the compounds of the present invention may be produced by a conventional process, namely, by the same process as described in the present specification.

EXAMPLE 1

Synthesis of 2-aminobenzaldehyde

A solution of 2-nitrobenzaldehyde (50 g, 0.33 mol) in tetrahydrofuran (0.33 liter) was added dropwise to an aqueous solution (1.2 liters) of sodium dithionite (230 g, 1.32 mols) and sodium carbonate (1.68 g, 1.59 mols) under ice-cooling over a period of 2 hours while maintaining the internal temperature at 10° C. or lower. After 30 minutes, the reaction solution was extracted with ethyl acetate and the extract solution was washed with water and then dried over anhydrous sodium sulfate. The organic solvent was removed by concentration under reduced pressure to obtain the desired compound (26 g, 64%) as an yellow oil.

$^1$H-NMR (200 MHzFT, TMS, CDCl$_3$); 6.13 (2H, brs), 6.65 (1H, d, J=8.5 Hz), 6.74 (1H, dt, J=1.0 Hz, 7.8 Hz), 7.31 (1H, ddd, J=1.6 Hz, 7.8 Hz, 8.5 Hz), 7.47 (1H, dd, J=1.6 Hz, 7.8 Hz), 9.86 (1H, s).

EXAMPLE 2

Synthesis of 2-benzyl-1,2,3,4-tetrahydrobenzo[b][1,6]-naphthyridine

A 10% potassium hydroxide/ethanol solution (120 ml) was added dropwise to a solution of 2-aminobenzaldehyde (26 g, 0.21 mol) and 1-benzyl-4-piperidone (40 g, 0.21 mol) in absolute ethanol (430 ml) over a period of 1 hour. After stirring overnight, the reaction solution was concentrated under reduced pressure and extracted with ethyl acetate, and the extract solution was washed with water and then dried over anhydrous sodium sulfate. The organic solvent was removed by concentration under reduced pressure, and the residue was recrystallized from ethyl acetate-isopropyl ether to obtain the desired compound (37 g, 63%) as white crystals.

$^1$H-NMR (200 MHzFT, TMS, CDCl$_3$); 2.95 (2H, t, J=6.1 Hz), 3.26 (2H, t, J=6.1 Hz), 3.75 (2H, s), 3.81 (2H, s), 7.24–7.77 (9H, complex), 7.94–8.03 (1H, m).

EXAMPLE 3

Synthesis of 1,2,3,4,6,7,8,9-octahydrobenzo[b][1,6]-naphthyridine

Platinum oxide (850 mg) was added to a solution of 2-benzyl-1,2,3,4-tetrahydrobenzo[b][1,6]-naphthyridine (8.5 g, 31 mmol) in trifluoroacetic acid (155 ml), and catalytic reduction was carried out at 50° C. for 24 hours. The catalyst was removed by filtration and the filtrate was concentrated under reduced pressure. The residue was made basic with 6N sodium hydroxide and extracted with toluene. The extract solution was dried over anhydrous sodium sulfate, and the organic solvent was removed by concentration under reduced pressure and the residue was recrystallized from isopropyl ether to obtain the desired compound (5.3 g, 90%) as white crystals.

$^1$H-NMR (200 MHZFT, TMS, CDCl$_3$); 1.71–1.95 (4H, m), 2.03 (1H, s), 2.70 (2H, brt), 2.87 (4H, brt), 3.20 (2H, t, J=6.1 Hz), 3.94 (2H, s), 6.99 (1H, s).

EXAMPLE 4

Synthesis of 1,2,3,4-tetrahydro-benzo[b][1,6]-naphthyridine

2-Benzyl-1,2,3,4-tetrahydro-benzo[b][1,6]-naphthyridine (4.4 g, 16.04 mmol) was dissolved in methanol (88 ml), followed by adding thereto acetic acid (1.84 ml, 32.08 mmol) and palladium-carbon (440 mg), and catalytic reduction was carried out overnight at 50° C. The catalyst was filtered off and the filtrate was neutralized with potassium carbonate and filtered. The organic layer thus obtained was concentrated under reduced pressure and the residue was purified by a silica gel column chromatography (methylene chloride/methanol=30/1 to 10/1) to obtain the desired compound (1.1 g, 37.2%) as a brown solid.

$^1$H-NMR (200 MHzFT, TMS, CDCl$_3$); 3.17 (2H, t, J=3.0 Hz), 3.34 (2H, t, J=5.8 Hz), 4.22 (2H, s), 7.42–7.50 (1H, m), 7.64 (1H, ddd, J=1.6, 6.9, 16.9 Hz), 7.72 (1H, brd), 7.78 (1H, brs), 7.99 (1H, d, J=8.1 Hz).

MS (FAB, m-NBA) m/z→185 [M+H]$^+$.

EXAMPLE 5

Synthesis of 2-t-butoxycarbonyl-1,2,3,4-tetrahydro-benzo[b][1,6]-naphthyridine-10-carboxamide Isatin (3.99 g, 20 mmol) and 1-t-butoxy-carbonyl-4-piperidone (2.94 g, 20 mmol) were dissolved in N,N-dimethylformamide (20 ml), followed by adding thereto ammonium acetate (4.63 g, 60 mmol), and the resulting mixture was stirred at 120° C. for 3 hours. The solvent was removed by concentration under reduced pressure, and acetone (20 ml) and water (20 ml) were added to the residue. The resulting slurry was filtered and the solid thus obtained was purified by suspension in ethyl acetate/hexane to obtain the desired compound (3.34 g, 50%) as a light-brownish-white solid.

$^1$H-NMR (200 MHzFT, TMS, CDCl$_3$); 1.47 (9H, s), 3.22 (2H, t, J=6.2 Hz), 3.83 (2H, t, J=6.2 Hz), 4.83 (2H, s), 6.26 (2H, brs), 7.51–7.61 (1H, m), 7.66–7.77 (1H, m), 7.90–7.97 (1H, m), 8.02 (1H, d, J=8.1 Hz).

MS (FAB, m-NBA) m/z 328→[M+H]$^+$.

EXAMPLE 6

Synthesis of 1,2,3,4-tetrahydro-benzo[b][1,61]-naphthyridine-10-carboxamide dihydrochloride 2-t-Butoxycarbonyl-1,2,3,4-tetrahydro-benzo[b][1,6]-naphthyridine-10-carboxamide (146 mg, 0.442 mmol) was suspended in dioxane (1 ml), followed by adding thereto 4N-hydrogen chloride/dioxane (2.2 ml, 8.83 mmol) under ice-cooling, and the resulting mixture was stirred at room temperature for 3 hours. The reaction mixture was concentrated to obtain the desired compound (146 mg, quant.) as a light-brown solid.

$^1$H-NMR (200 MHZFT, TMS, CD$_3$OD); 3.62–3.88 (4H, complex), 4.69 (2H, s), 7.87–8.01 (1H, m), 8.10–8.26 (3H, complex).

MS (FAB, m-NBA) m/z 228→[M+H]+.

EXAMPLE 7

Synthesis of 2-t-butoxycarbonyl-1,2,3,4-tetrahydro-benzo[b][1,6]-naphthyridine-10-carboxylic acid Isatin (14.71 g, 100 mmol) and 1-t-butoxycarbonyl-4-piperidone (19.93 g, 100 mmol) were dissolved in ethanol (200 ml), followed by adding thereto an ethanolic solution (50 ml) of KOH (12.34 mg), and the resulting mixture was stirred at 70° C. for 24 hours. The solvent was removed by concentration under reduced pressure, and the residue was neutralized with acetic acid. The resulting insoluble material was purified by suspension in methanol to obtain the desired compound (9.5 g, 29%) as a light-brownish-white substance.

$^1$H-NMR (200 MHzFT, TMS, DMSO-$d_6$); 1.41 (9H, s), 3.14 (2H, t, J=6.2 Hz), 3.76 (2H, t, J=6.2 Hz), 4.74 (2H, s), 7.56–7.68 (1H, m), 7.68–7.80 (1H, m), 7.86 (1H, d, J=8.4 Hz), 7.98 (1H, d, J=8.4 Hz). MS (FAB, m-NBA) m/z 329→[M+H]$^+$.

EXAMPLE 8

Synthesis of 2-t-butoxycarbonyl-10-methoxycarbonyl-1,2,3,4-tetrahydro-benzo[b][1,6]-naphthyridine 2-t-Butoxycarbonyl-1,2,3,4-tetrahydro-benzo[b][1,6]-naphthyridine-10-carboxylic acid (500 mg, 1.523 mmol) was dissolved in N,N-dimethylformamide (3 ml), followed by adding thereto potassium carbonate (315.1 mg, 2.28 mmol) and methyl iodide (0.13 ml, 2.06 mmol), and the resulting mixture was stirred overnight at room temperature. Water was added to the reaction mixture, followed by extraction with ethyl acetate. The organic layer was washed with a saturated aqueous sodium chloride solution, dried over anhydrous sodium sulfate and then concentrated under reduced pressure, and the resulting residue was purified by a silica gel column chromatography (hexane/ethyl acetate= 1/1) to obtain the desired compound (487 mg, 93.4%) as a brown oil.

$^1$H-NMR (200 MHzFT, TMS, CDCl$_3$); 1.50 (9H, s), 3.24 (2H, t, J=6.1 Hz), 3.84 (2H, t, J=6.2 Hz), 4.09 (3H, s), 4.80 (2H, s), 7.50–7.60 (1H, m), 7.67–7.77 (1H, m), 7.78–7.87 (1H, m), 8.03 (1H, d, J=8.1 Hz).

EXAMPLE 9

Synthesis of 10-methoxycarbonyl-1,2,3,4-tetrahydro-benzo[b][1,6]naphthyridine dihydrochloride The title compound was obtained in the same manner as in Example 6.

$^1$H-NMR (200 MHzFT, TMS, CD$_3$OD); 3.70–3.87 (4H, complex), 4.21 (3H, s), 4.77 (2H, s), 7.92–8.03 (1H, m), 8.12–8.32 (3H, complex).

EXAMPLE 10

Synthesis of 10-amino-2-t-butoxycarbonyl-1,2,3,4-tetrahydro-benzo[b][1,6]-naphthyridine 1-t-Butoxycarbonyl-4-piperidone (1.69 g, 8.46 mmol), zinc chloride (1.50 g, 11.0 mmol) and 2-aminobenzonitrile (1.0 g, 8.46 mmol) were mixed and then reacted at 90° C. for 1 hour. The reaction mixture was cooled to room temperature to obtain a solid, which was ground together with toluene and filtered. The thus treated solid was suspended in chloroform and concentrated aqueous ammonia was added thereto and stirred. The chloroform layer was separated, dried over anhydrous sodium sulfate and then concentrated to obtain the desired compound (0.54 g, 1.8 mmol, 21%).

$^1$H-NMR (200 MHzFT, TMS, CDCl$_3$); 1.53 (9H, s), 3.10 (2H, t, J=5.9 Hz), 3.80 (2H, t, J=5.8 Hz), 4.53 (2H, s), 4.70 (2H, br.s.), 7.35–7.50 (1H, m), 7.55–7.68 (1H, m), 7.73 (1H, d, J=8.3 Hz), 7.91 (1H, d, J=7.7 Hz).

MS (FAB, m-NBA) m/z→300 [M+H]$^+$, 599[2M+H]$^+$.

EXAMPLE 11

Synthesis of 10-amino-1,2,3,4-tetrahydro-benzo[b][1,6]-naphthyridine trihydrochloride 10-Amino-2-t-butoxycarbonyl-1,2,3,4-tetrahydro-benzo[b][1,6]-naphthyridine (0.538 g, 1.80 mmol) was suspended in dioxane (3 ml), followed by adding thereto 4N-hydrogen chloride/dioxane (9 ml) under ice-cooling, and the resulting mixture was stirred at room temperature for 1 hour. The reaction mixture was concentrated to obtain the desired compound (0.585 g, quant.).

$^1$H-NMR (200 MHzFT, TMS, CD$_3$); 3.35–3.45 (2H, m), 3.62–3.78 (2H, m), 4.35 (2H, s), 7.66–7.76 (1H, m), 7.85–7.87 (1H, m), 7.93–8.03 (1H, m), 8.37–8.45 (1H, m). MS (FAB, m-NBA) m/z→200 [M+H]$^+$,

EXAMPLE 12

Synthesis of 2-t-butoxycarbonyl-10-hydroxymethyl-1,2,3,4-tetrahydro-benzo[b][1,6]-naphthyridine Methyl 2-t-butoxycarbonyl-1,2,3,4-tetrahydro-benzo[b][1,6]-naphthyridine-10-carboxylate (1.14 g, 3.05 mmol) was dissolved in ethanol (3 ml), followed by adding thereto sodium tetrahydroborate (138.4 mg, 3.66 mmol) and then a solution of calcium chloride (338.5 mg, 3.05 mmol) in ethanol (3 ml) under ice-cooling, and the resulting mixture was stirred at room temperature for 4 hours and then at 60° C. for 3 hours. A saturated aqueous ammonium chloride solution was added to the reaction mixture, followed by extraction with ethyl acetate. The organic layer was washed with a saturated aqueous sodium chloride solution, dried over anhydrous sodium sulfate and then concentrated under reduced pressure, and the resulting residue was purified by a silica gel column chromatography (hexane/ethyl acetate= 1/1) to obtain the desired compound (442 mg, 46%) as a yellow oil.

$^1$H-NMR (200 MHzFT, TMS, CDCl$_3$); 1.49 (9H, s), 3.21 (2H, t, J=6.2 Hz), 3.81 (2H, t, J=6.2 Hz), 4.92 (2H, s), 5.13 (2H, s), 7.50–7.60 (1H, m), 7.63–7.73 (1H, m), 7.97–8.05 (1H, m), 8.14–8.22 (1H, m).

MS (FAB, m-NBA) m/z 315→-[M+H]$^+$.

EXAMPLE 13

Synthesis of 10-hydroxymethyl-1,2,3,4-tetrahydro-benzo[b][1,6]-naphthyridine dibenzenesulfonate 2-t-Butoxycarbonyl-10-hydroxymethyl-1,2,3,4-tetrahydro-benzo[b][1,6]-naphthyridine (202 mg, 0.643 mmol) was dissolved in methanol (1.3 ml), followed by adding thereto benzenesulfonic acid monohydrate (226.3 mg, 1.285 mmol), and the resulting mixture was heated under reflux at 70° C. for 3 hours. The reaction mixture was cooled to room temperature and then concentrated under reduced pressure to obtain the desired compound (361.2 mg, quant.) as a brown substance.

¹H-NMR (200 MHzFT, TMS, CD₃OD); 3.58–3.85 (4H, complex), 4.97 (2H, s), 5.22 (2H, s), 7.24–7.45 (6H, m), 7.64–7.80 (4H, m), 7.90–8.01 (1H, m), 8.09–8.16 (2H, complex), 8.59 (1H, d, J=8.6 Hz).

MS (FAB, m-NBA) m/z 215→[M+H]⁺.

EXAMPLE 14

Synthesis of 2-t-butoxycarbonyl-10-acetylamino-1,2,3,4-tetrahydro-benzo[b][1,6]-naphthyridine 10-Amino-2-t-butoxycarbonyl-1,2,3,4-tetrahydro-benzo[b][1,6]-naphthyridine (0.77 g, 2.59 mmol) was added to pyridine (1.0 g, 12.7 mmol). Acetic anhydride (0.53 g, 5.18 mmol) was added to the mixture, followed by refluxing for 7.5 hours. Then, water was added thereto and the resulting mixture was extracted with chloroform. The chloroform layer was dried over anhydrous sodium sulfate and the solvent was distilled off under reduced pressure. The resulting residue was purified by a silica gel column chromatography to obtain the desired compound (0.5 g, 1.47 mmol, 57%).

¹H-NMR (200 MHzFT, TMS, CDCl₃); 1.49 (9H, s), 2.36 (3H, s), 3.16 (2H, t, J=5.9 Hz), 3.82 (2H, t, J=6.2 Hz), 4.67 (2H, s), 7.43–7.53 (1H, m), 7.60–7.71 (1H, m), 7.87 (1H, d, J=8.3 Hz), 7.98 (1H, d, J=8.4 Hz). MS (FAB, m-NBA) m/z→342 [M+H]⁺, 683.6 [2M+H]⁺.

EXAMPLE 15

Synthesis of 10-acetylamino-1,2,3,4-tetrahydro-benzo[b][1,6]-naphthyridine dihydrochloride 10-Methylcarbonylamino-2-t-butoxycarbonyl-1,2,3,4-tetrahydro-benzo[b][1,6]-naphthyridine (0.5 g, 1.47 mmol) was suspended in a mixture of dioxane (4.5 ml) and methanol (1 ml), followed by adding thereto 4N-hydrogen chloride/dioxane (7.35 ml) under ice-cooling, and the resulting mixture was stirred at room temperature for 1.5 hours. The reaction mixture was concentrated to obtain the desired compound (0.369 g, quant.).

¹H-NMR (200 MHZFT, TMS, CD₃OD); 2.44 (3H, s), 3.68–3.87 (4H, m), 4.47 (2H, s), 7.93–8.03 (1H, m), 8.17–8.22 (2H, m), 8.45 (1H, d, J=8.5 Hz). MS (FAB, m-NBA) m/z→242 [M+H]⁺.

EXAMPLE 16

Synthesis of 2-benzyl-10-phenyl-1.2.3.4-tetrahydro-benzo[b][1,6]-naphthyridine 1-t-Butoxycarbonyl-4-piperidone (1.93 g, 10.2 mmol) and 2-aminobenzophenone (2.01 g, 10.2 mmol) were suspended in acetic acid (10 ml), followed by adding thereto sulfuric acid (0.1 ml), and the reaction was carried out at 120° C. for 1 hour. The reaction mixture was poured into cold aqueous ammonia, and the crystals precipitated were washed with water and recrystallized from ethanol to obtain the desired compound (2.60 g, 7.43 mmol).

¹H-NMR (200 MHzFT, TMS, CDCl₃); 2.84 (2H, t, J=6.1 Hz), 3.28 (2H, t, J=6.0 Hz), 3.56 (2H, s), 3.60 (2H, s), 7.20–7.37 (10H, m), 7.45–7.55 (2H, m), 7.57–7.67 (1H, m), 8.03 (1H, d, J=8.4 Hz). MS (FAB, m-NBA) m/z→351 [M+H]⁺.

EXAMPLE 17

Synthesis of 10-phenyl-1,2,3,4-tetrahydro-benzo[b][1,6]-naphthyridine

Palladium black (125 mg) was added to a solution of 2-benzyl-10-phenyl-1,2,3,4-tetrahydro-benzo[b][1,6]-naphthyridine (1.25 g, 3.57 mmol) in acetic acid (9 ml), and the resulting mixture was stirred under a hydrogen atmosphere for 9 hours. The catalyst was removed by filtration and the filtrate was concentrated under reduced pressure. The residue was made basic with 1N sodium hydroxide and extracted with diethyl ether. The extract solution was dried over anhydrous sodium sulfate and concentrated under reduced pressured to be freed of the solvent, and the residue was washed with diethyl ether to obtain the desired compound (0.45 g, 1.75 mmol, 49%).

¹H-NMR (200 MHZFT, TMS, CDCl₃); 3.20–3.36 (4H, m), 3.86 (2H, s), 7.21–7.28 (3H, m), 7.33–7.38 (2H, m), 7.45–7.68 (1H, m), 8.04 (1H, d, J=8.4 Hz). MS (FAB, m-NBA) m/z→261 [M+H]⁺.

EXAMPLE 18

Synthesis of 2-t-butoxycarbonyl-10-methoxycarbonylamino-1,2,3,4-tetrahydro-benzo[b][1,6]-naphthyridine 2-t-Butoxycarbonyl-1,2,3,4-tetrahydro-benzo[b][1,6]-naphthyridine-10-carboxamide (0.5 g, 1.53 mmol) was added to a solution of sodium (0.078 g, 3.37 mmol) in methanol (31 ml), and bromine (0.245 g, 1.53 mmol) was added dropwise thereto while maintaining the temperature at 25° C. or lower. After completion of the dropwise addition, the resulting mixture was heated under reflux for 30 minutes. Water was added to the reaction mixture, followed by extraction with ethyl acetate. The ethyl acetate layer was dried over anhydrous sodium sulfate and concentrated under reduced pressure, and the residue was purified by a silica gel chromatography (hexane-ethyl acetate=1 : 1) to obtain the desired compound (0.46 g, 1.28 mmol, 84%).

¹H-NMR (200 MHzFT, TMS, CDCl₃); 1.49 (9H, s), 3.23 (2H, t, J=6.1 Hz), 3.81 (3H, s), 3.84 (2H, t, J=6.3 Hz), 4.75 (2H, s), 6.85–7.05 (1H, br.s.), 7.48–7.58 (1H, m), 7.63–7.74 (1H, m), 7.90 (1H, d, J=8.4 Hz), 8.02 (1H, d, J=8.4 Hz). MS (FAB, m-NBA) m/z→358 [M+H]⁺, 715 [2M+H]⁺.

EXAMPLE 19

Synthesis of 10-methoxycarbonylamino-1,2,3,4-tetrahydro-benzo[b][1,6]-naphthyridine dihydrochloride The desired compound was obtained in the same manner as in Example 6.

¹H-NMR (200 MHzFT, TMS, CD₃OD); 3.68–3.87 (4H, m), 3.92 (3H, s), 4.56 (2H, s), 7.90–8.01 (1H, m), 8.15–8.20 (2H, m), 8.37–8.45 (1H, m). MS (FAB, m-NBA) m/z→258 [M+H]⁺.

EXAMPLE 20

Synthesis of 2-t-butoxycarbonyl-10-N-methylmethoxycarbonylamino-1,2,3,4-tetrahydro-benzo[b][1,6]-naphthyridine Sodium hydride (0.038 g, 0.95 mmol) was suspended in dimethylformamide (3 ml), and 2-t-butoxycarbonyl-10-methoxycarbonylamino-1,2,3,4-tetrahydro-benzo[b][1,6]-naphthyridine (0.225 g, 0.63 mmol) was added thereto. After stirring for 30 minutes, methyl iodide (0.143 g, 1.01 mmol) was added thereto and stirred overnight. Water was added to the reaction mixture, followed by extraction with ethyl acetate. The ethyl acetate layer was dried over anhydrous sodium sulfate and concentrated under reduced pressure, and the residue was purified by a silica gel chromatography (hexane-ethyl acetate-methanol=10:10:1) to obtain the desired compound (0.164 g, 0.44 mmol, 70%).

$^1$H-NMR (200 MHzFT, TMS, CDCl$_3$); 1.50 (9H, s), 3.24 (2H, t, J=6.0 Hz), 3.31 (3H, s), 3.61 (2H, s), 3.65–4.14 (3H, m), 4.46–4.90 (2H, complex), 7.49–7.60 (1H, m), 7.64–7.79 (2H, m), 8.02–8.10 (1H, m). MS (FAB, m-NBA) m/z→358 [M+H]$^+$, 715 [2M+H]$^+$.

EXAMPLE 21

Synthesis of N-methyl-10-methoxycarbonylamino-1,2,3,4-tetrahydro-benzo[b][1,6]-naphthyridine dihydrochloride The desired compound was obtained in the same manner as in Example 6.

$^1$H-NMR (200 MHzFT, TMS, CD$_3$OD); 3.35–3.52 (3H, m), 3.64–3.96 (7H, complex), 4.45–4.78 (2H, m), 7.90–8.02 (1H, m), 8.05–8.20 (2H, m), 8.36–8.45 (1H, m). MS (FAB, m-NBA) m/z→272 [M+H]$^+$.

EXAMPLE 22

Synthesis of 2-benzyl-10-chloro-1,2,3,4-tetrahydro-benzo[b][1,6]-naphthyridine

Anthranilic acid (9.6 g, 70 mmol) and 1-benzyl-4-piperidone (13.2 g, 70 mmol) were suspended in phosphorus oxychloride (65.2 ml, 700 mmol), and the suspension was heated under reflux for 4 hours. The excess phosphorus oxychloride was removed by distillation and the concentrated residue was carefully added to 28% aqueous ammonia under ice-cooling and extracted with chloroform. The organic layer was washed with water, dried over anhydrous sodium sulfate and then concentrated under reduced pressure, and the resulting residue was purified by a silica gel column chromatography (hexane/ethyl acetate/methanol=30:10:1) to obtain the desired compound (13 g, 60%) as a light-yellowish-white substance.

$^1$H-NMR (200 MHzFT, TMS, CDCl$_3$); 2.90 (2H, t, J=6.0 Hz), 3.24 (2H, t, J=6.0 Hz), 3.82 (2H, s), 3.93 (2H, s), 7.27–7.46 (5H, m), 7.50–7.61 (1H, m), 7.64–7.74 (1H, m), 7.96–8.03 (1H, m), 8.12–8.20 (1H, m).

MS (FAB, m-NBA) m/z 309, 311→[M+H]$^+$.

EXAMPLE 23

Synthesis of 10-chloro-1,2,3,4-tetrahydro-benzo[b][1,6]-naphthyridine

2-Benzyl-10-chloro-1,2,3,4-tetrahydro-benzo[b][1,6]-naphthyridine (1.54 g, 5 mmol) was dissolved in methylene chloride, followed by adding thereto 1-chloroethyl chloroformate (0.81 ml, 7.5 mmol) under ice-cooling, and the resulting mixture was stirred at room temperature for 1 hour. The reaction mixture was concentrated and methanol (20 ml) was added to the residue, and the resulting mixture was heated under reflux at 80° C. for 1 hour. The reaction mixture was concentrated and a 1N-aqueous potassium hydroxide solution was added thereto, followed by extraction with methylene chloride. The organic layer was dried over anhydrous sodium sulfate and then concentrated under reduced pressure, and the resulting residue was purified by suspension in diethyl ether/hexane to obtain the desired compound (656.4 mg, 60%) as a light-yellowish-white substance.

$^1$H-NMR (200 MHzFT, TMS, CDCl$_3$); 3.08–3.18 (2H, m), 3.23–3.33 (2H, m), 4.23 (2H, s), 7.50–7.60 (1H, m), 7.63–7.73 (1H, m), 7.95–8.02 (1H, m), 8.11–8.18 (1H, m). MS (FAB, m-NBA) m/z 219, 221→[M+H]$^+$.

EXAMPLE 24

Synthesis of 2-[(–)-4-(N-benzoyl-N-methyl)amino-3-(3.4-dichlorophenyl)butyll-1,2,3,4,6,7,8,9-octahydro-benzo[b][1,6]naphthyridine 2-Benzyl-1,2,3,4-tetrahydrobenzo[b][1,6]-naphthyridine (545 mg, 2.9 mmol) was added to a solution of (–)-4-(N-benzoyl-N-methyl)amino-3-(3,4-dichlorophenyl)butanol (675 mg, 1.9 mmol) in methanol (6 ml) and stirred for 3 hours. Then, a solution of sodium cyanotrihydroborate (383 mg, 6.1 mmol) in tetrahydrofuran (6 mml) was added thereto and stirred overnight. To the reaction mixture was added 1N sodium hydroxide, followed by extraction with ethyl acetate. The extract solution was washed with distilled water and a saturated aqueous sodium chloride solution and then dried over anhydrous sodium sulfate. The organic solvent was removed by concentration under reduced pressure and the resulting residue was purified by a silica gel column chromatography (chloroform/methanol=100:1→30:1) to obtain the desired compound (204 mg, 20%).

$^1$H-NMR (200 MHzFT, TMS, CDCl$_3$); 1.4–4.2 (22H, complex), 6.7–7.5 (9H, complex). MS (FAB, m-NBA) m/z 522, 524→[M+H]$^+$.

EXAMPLE 25

Synthesis of 2-[(–)-4-(N-benzoyl-N-methyl)amino-3-(3,4-dichlorophenyl butyll-1,2,3,4,6,7,8,9-octahydro-benzo[b][1,6]naphthyridine fumarate Fumaric acid (45 mg, 0.39 mmol) was dissolved in ethanol (0.5 ml), followed by adding thereto a solution of 2-[(–)-4-(N-benzoyl-N-methyl)amino-3-(3,4-dichlorophenyl)butyl]-1,2,3,4,6,7,8,9-octahydro-benzo[b][1,6]naphthyridine (204 mg, 0.39 mmol) in ethanol (1 ml). After 1 hour, the reaction solution was concentrated under reduced pressure and recrystallized from chloroform-diethyl ether to obtain the desired compound (87 mg, 35%).

$^1$H-NMR (200 MHzFT, TMS, CDCl$_3$); 1.7–4.2 (22H, complex), 6.68 (2H, s), 6.9–7.7 (8H, complex). MS (FAB, m-NBA) m/z 522, 524, 526→[M+H]$^+$.

EXAMPLE 26

Synthesis of 2-[(–)-4-(N-benzoyl-N-methyl)amino-3-(3,4-dichlorophenyl)butyl]-10-methylcarbonylamino-1,2,3,4-tetrahydro-benzo[b][1,6]naphthyridine (–)-4-(N-benzoyl-N-methyl)amino-3-(3,4-dichlorophenyl)butyl benzenesulfonate (0.57 g, 1.16 mmol) and triethylamine (0.13 g, 1.28 mmol) were added to a solution of 10-methylcarbonylamino-1,2,3,4-tetrahydro-benzo b][1,6]-naphthyridine (0.281 g, 1.16 mmol) in a mixture of tetrahydrofuran (5 ml) and dimethyl sulfoxide (1 ml), and the resulting mixture was stirred at room temperature for 5 hours and then at 70° C. for 4 hours. Water was added to the reaction mixture, followed by extraction with ethyl acetate. The ethyl acetate layer was dried over anhydrous sodium sulfate and concentrated under reduced pressure, and the residue was purified by a silica gel chromatography (chloroform-methanol=30:1) to obtain the desired compound (0.393 g, 0.683 mmol, 59%).

$^1$H-NMR (200 MHzFT, TMS, CDCl$_3$); 1.20–4.10 (19H, complex), 6.70–7.90 (10H, complex), 7.99 (1H, br.d.), 8.12 (1H, br.s.). MS (FAB, m-NBA) m/z 575, 577→[M+H]$^+$.

EXAMPLE 27

Synthesis of 2-[(−)-4-(N-benzoyl-N-methyl)amino-3-(3-4-dichlorophenyl butyl]-10-methylcarbonylamino-1,2,3,4-tetrahydro-benzo[b][1,6]naphthyridine fumarate Fumaric acid (0.067 g, 0.574 mmol) was dissolved in ethanol (1 ml) and the resulting solution was added to a solution of 2-[(−)-4-(N-benzoyl-N-methyl)amino-3-(3,4-dichlorophenyl)butyl]-10-methyl-carbonylamino-1,2,3,4-tetrahydro-benzo[b][1,6]-naphthyridine (0.330 g, 0.574 mmol) in ethanol (2 ml). After 1 hour, the reaction solution was concentrated under reduced pressure to obtain the desired compound (0.267 g).

$^1$H-NMR (200 MHzFT, TMS, CD$_3$OD); 2.02–4.06 (19H, complex), 6.72 (2H, s), 6.92–7.23 (2H, complex), 7.28–7.82 (8H, complex), 7.87–8.05 (2H, complex). MS (FAB, m-NBA) m/z 575, 577→[M+H]$^+$.

EXAMPLE 28

Synthesis of 2-[(−)-4-(N-benzoyl-N-methyl)amino-3-(3,4-dichlorophenyl)butyl]-1,2,3,4-tetrahydro-benzo-[b][1,6]naphthyridine-10-carboxamide The title compound was obtained in the same manner as in Example 26.

$^1$H-NMR (200 MHzFT, TMS, CDCl$_3$); 1.21–4.10 (16H, complex), 6.27–7.58 (11H, complex), 7.66 (1H, brs), 7.83 (1H, d, J=8.1 Hz), 7.98 (1H, d, J=8.4 Hz). MS (FAB, m-NBA) m/z 561, 563→[M+H]$^+$.

EXAMPLE 29

Synthesis of 2-[(−)-4-(N-benzoyl-N-methyl)amino-3-(3,4-dichlorophenyl)butyl]-1,2,3,4-tetrahydro-benzo-[b][1,6]naphthyridine-10-carboxamide fumarate The title compound was obtained in the same manner as in Example 27.

$^1$H-NMR (200 MHzFT, TMS, CD$_3$OD); 1.28–4.18 (16H, complex), 6.71 (2H, s), 6.71–8.02 (12H, complex).

MS (FAB, m-NBA) m/z 561, 563 →[M+H]$^+$.

EXAMPLE 30

Synthesis of 2-[(−)-4-(N-benzoyl-N-methyl)amino-3-(3,4-dichlorophenyl butyl]-10-methoxycarbonyl-1,2,3,4-tetrahydro-benzo-[b][1,6]naphthyridine The title compound was obtained in the same manner as in Example 26.

$^1$H-NMR (200 MHzFT, TMS, CDCl$_3$); 1.60–4.01 (16H, complex), 4.06 (3H, s), 6.72–8.08 (12H, complex). MS (FAB, M-NBA) m/z 576, 578→[M+H]$^+$.

EXAMPLE 31

Synthesis of 2-[(−)-4-(N-benzoyl-N-methyl amino-3-(3,4-dichlorophenyl)butyl]-10-methoxycarbonyl-1,2,3,4-tetrahydro-benzo[b][1,6]naphthyridine fumarate The title compound was obtained in the same manner as in Example 27.

$^1$H-NMR (200 MHzFT, TMS, CD$_3$OD); 1.60–4.20 (19H, complex), 6.72 (2H, s), 6.85–8.05 (12H, complex).

MS (FAB, m-NBA) m/z 576, 578 →[M+H]$^+$.

EXAMPLE 32

Synthesis of 2-[(−)-4-(N-benzoyl-N-methyl)amino-3-(3,4-dichlorophenyl butyl]-1,2,3,4-tetrahydro-benzo-[b][1,6]naphthyridine-10-carboxylic acid Methyl 2-[(−)-4-(N-benzoyl-N-methyl)amino-3-(3,4-dichlorophenyl)butyl]-1,2,3,4-tetrahydro-benzo-[b][1,6]naphthyridine-10-carboxylate (166.6 mg, 0.289 mmol) was dissolved in methanol (5 ml), followed by adding thereto a 1N-aqueous sodium hydroxide solution under ice-cooling, and the resulting mixture was stirred at room temperature for 2 hours and then at 70° C. for 3 hours. After the reaction mixture was allowed to cool to room temperature, a 2M-aqueous oxalic acid solution was added thereto, followed by extraction with methylene chloride. The organic layer was dried over anhydrous sodium sulfate and then concentrated under reduced pressure to obtain the desired compound (97 mg, 58.4%) as a yellow solid.

MS (FAB, m-NBA); m/z 562, 564→[M+H]$^+$.

EXAMPLE 33

Synthesis of 2-[(−)-4-(N-benzoyl-N-methyl)amino-3-(3,4-dichlorophenyl)butyl]-1,2,3,4-tetrahydro-benzo-[b][1,6]naphthyridine-10-carboxylic acid fumarate The title compound was obtained in the same manner as in Example 27.

$^1$H-NMR (200 MHzFT, TMS, CD$_3$OD); 1.80–4.60 (16H, complex), 6.75 (2H, s), 6.70–8.10 (12H, complex). MS (ESI) m/z 562, 564, 566→[M+H]$^+$.

EXAMPLE 34

Synthesis of 10-amino-2-[(−)-4-(N-benzoyl-N-methyl)amino-3-(3,4-dichlorophenyl)butyl]-1,2,3,4-tetrahydro-benzo[b][1,6]naphthyridine The title compound was obtained in the same manner as in Example 26.

$^1$H-NMR (200 MHzFT, TMS, CDCl$_3$); 1.25–4.10 (16H, complex), 4.58 (2H, br.s.), 7.08–7.50 (9H, complex), 7.50–7.09 (2H, m), 7.86–8.04 (1H, m). MS (FAB, m-NBA) m/z→533, 535 [M+H]$^+$.

EXAMPLE 35

Synthesis of 10-amino-2-[(−)-4-(N-benzoyl-N-methyl)amino-3-(3,4-dichlorophenyl)butyl]-1,2,3,4-tetrahydro-benzo[b][1,6]naphthyridine fumarate The title compound was obtained in the same manner as in Example 27.

$^1$H-NMR (200 MHzFT, TMS, CD$_3$OD); 1.70–3.89 (16H, complex), 6.71 (2H, s), 6.91–7.20 (2H, complex), 7.35–7.80 (8H, complex), 7.82–7.88 (1H, m), 8.34 (1H, br.d.).

MS (FAB, m-NBA) m/z→533, 535 (M+H]$^+$.

EXAMPLE 36

Synthesis of 2-[(−)-4-(N-benzoyl-N-methyl)amino-3-(3,4-dichlorophenyl)butyl]-10-hydroxymethyl-1.2,3,4-tetrahydro-benzo-[b][1,6]naphthyridine The title compound was obtained in the same manner as in Example 26.

¹H-NMR (200 MHzFT, TMS, CDCl₃); 1.25–4.28 (16H, complex), 5.03 (2H, s), 6.71–7.75 (10H, complex), 7.99 (1H, brd), 8.17 (1H, brd). MS (ESI) m/z 548, 550, 552→[M+H]⁺.

EXAMPLE 37

Synthesis of 2-[(−)-4-(N-benzoyl-N-methyl)amino-3-(3,4-dichlorophenyl butyl]-10-hydroxymethyl-1,2,3,4-tetrahydro-benzo-[b][1,6]naphthyridine fumarate The title compound was obtained in the same manner as in Example 27.

¹H-NMR (200 MHzFT, TMS, CD₃OD); 1.70–5.12 (19H, complex), 6.72 (2H, s), 6.80–7.90 (10H, complex). 7.95 (1H, brd), 8.27 (1H, brd). MS (FAB, m-NBA) m/z 548, 550→[M+H]⁺.

EXAMPLE 38

Synthesis of 2-[(−)-4-(N-benzoyl-N-methyl)amino-3-(3,4-dichlorophenyl)butyl]-10-phenyl-1,2,3,4-tetrahydro-benzo[b][1,6]naphthyridine The title compound was obtained in the same manner as in Example 26.

¹H-NMR (200 MHzFT, TMS, CDCl₃); 1.59–3.95 (16H, complex), 6.60–7.69 (16H, complex), 8.03 (1H, br.s.). MS (FAB, m-NBA) m/z→594, 596 [M+H]⁺.

EXAMPLE 39

Synthesis of 2-[(−)-4-(N-benzoyl-N-methyl)amino-3-(3,4-dichlorophenyl)butyl]-10-phenyl-1,2,3,4-tetrahydro-benzo[b][1,6]naphthyridine fumarate The title compound was obtained in the same manner as in Example 27.

¹H-NMR (200 MHzFT, TMS, CD₃OD); 1.50–3.85 (16H, complex), 6.71 (2H, s), 6.80–7.78 (16H, complex), 7.99 (1H, br.d.).

MS (FAB, m-NBA) m/z→594, 596 [M+H]⁺.

EXAMPLE 40

Synthesis of 2-[(−)-4-(N-benzoyl-N-methyl)amino-3-(3,4-dichlorophenyl)butyl]-10-methoxycarbonylamino-1,2,3,4-tetrahydro-benzo[b][1,6]naphthyridine The title compound was obtained in the same manner as in Example 26.

¹H-NMR (200 MHzFT, TMS, CDCl³); 1.18–3.83 (19H, complex), 6.72–7.73 (10H, complex), 7.86 (1H, br.d.), 8.00 (1H, br.d.). MS (FAB, m-NBA) m/z→591, 593 [M+H]⁺.

EXAMPLE 41

Synthesis of 2-[(−)-4-(N-benzoyl-N-methyl)amino-3-(3,4-dichlorophenyl)butyl]-10-methoxycarbonylamino-1,2,3,4-tetrahydro-benzo[b][1,6]naphthyridine fumarate The title compound was obtained in the same manner as in Example 27.

¹H-NMR (200 MHzFT, TMS, CD₃OD); 0.84–4.17 (19H, complex), 6.72 (2H, s), 6.93–8.08 (12H, complex).

MS (FAB, m-NBA) m/z→591, 593 [M+H]⁺.

EXAMPLE 42

Synthesis of 2-[(−)-4-(N-benzoyl-N-methyl)amino-3-(3,4-dichlorophenyl)butyl]-10-(N-methyl-N-methoxycarbonyl)-amino-1,2,3,4-tetrahydro-benzo[b][1,6]naphthyridine The title compound was obtained in the same manner as in Example 26.

¹H-NMR (200 MHzFT, TMS, CDCl₃); 1.65–3.90 (22H, complex), 7.05–7.67 (11H, complex), 8.04 (1H, br.d.). MS (FAB, m-NBA) m/z→605, 607 [M+H]⁺.

EXAMPLE 43

Synthesis of 2-[(−)-4-(N-benzoyl-N-methyl)amino-3-(3,4-dichlorophenyl)butyl]-10-(N-methyl-N-methoxycarbonyl)-amino-1,2,3,4-tetrahydro-benzo[b][1,6]naphthyridine fumarate The title compound was obtained in the same manner as in Example 27.

¹H-NMR (200 MHzFT, TMS, CD₃OD); 0.82–3.88 (22H, complex), 6.74 (2H, s), 6.96–7.86 (11H, complex), 8.02 (1H, br.d.). MS (FAB, m-NBA) m/z→605, 607 [M+H]⁺.

EXAMPLE 44

Synthesis of 2-[(−)-4-(N-benzoyl-N-methyl)amino-3-(3,4-dichlorophenyl)butyl]-10-chloro-1,2,3,4-tetrahydro-benzo[b][1,6]naphthyridine The title compound was obtained in the same manner as in Example 26.

¹H-NMR (200 MHzFT, TMS, CDCl₃); 1.60–4.10 (16H, complex), 6.72–7.50 (8H, complex), 7.55–7.64 (1H, m), 7.65–7.80 (1H, m), 8.00 (1H, d, J=8.0 Hz), 8.18 (1H, dd, J=1.2, 8.4 Hz). MS (FAB, m-NBA) m/z 552, 554, 556→[M+H]⁺.

EXAMPLE 45

Synthesis of 2-[(−)-4-(N-benzoyl-N-methyl)amino-3-(3,4-dichlorophenyl)butyl]-10-chloro-1,2,3,4-tetrahydro-benzo[b][1,6]naphthyridine fumarate The title compound was obtained in the same manner as in Example 27.

¹H-NMR (200 MHzFT, TMS, CD₃OD); 1.50–4.12 (16H, complex), 6.73 (2H, s), 6.80–8.35 (12H, complex). MS (FAB, m-NBA) m/z 552, 554, 556→[M+H]⁺.

EXAMPLE 46

Synthesis of 10-benzoylamino-2-[(−)-4-(N-benzoyl-N-methyl)amino-3-(3,4-dichlorophenyl)butyl]1,2,3,4-tetrahydro-benzo-[b][1,6]naphthyridine The title compound was obtained in the same manner as in Example 26.

¹H-NMR (200 MHzFT, TMS, CDCl³); 1.40–4.10 (16H, complex), 6.68–8.60 (18H, complex). MS (FAB, m-NBA) m/z→637, 639 [M+H]⁺.

EXAMPLE 47

Synthesis of 10-benzoylamino-2-[(−)-4-(N-benzoyl-N-methyl)amino-3-(3,4-dichlorophenyl)butyl]-1,2,3,4-tetrahydro-benzo-[b][1,6]naphthyridine fumarate The title compound was obtained in the same manner as in Example 27.

¹H-NMR (200 MHzFT, TMS, CD³OD); 1.50–4.10 (16H, complex), 6.71 (2H, s), 6.80–8.18 (17H, complex). MS (FAB, M-NBA) m/z 637, 639→[M+H]⁺.

EXAMPLE 48

Synthesis of 10-acetylamino-2-[(−)-4-(N-benzoyl-N-methyl)amino-3-(3,4-dichlorophenyl)butyl]-1,2,3,4,6,7,8,9-octahydro-benzo-[b][1,6]naphthyridine The title compound was obtained in the same manner as in Example 26.

$^1$H-NMR (200 MHzFT, TMS, CDCl$^3$); 1.60–4.15 (27H, complex), 6.70–7.50 (9H, complex). MS (FAB, m-NBA) m/z 579, 581→[M+H]$^+$.

EXAMPLE 49

Synthesis of 10-acetylamino-2-[(−)-4-(N-benzoyl-N-methyl)amino-3-(3,4-dichlorophenyl)butyl]-1,2,3,4,6,7,8,9-octahydro-benzo-[b][1,6]naphthyridine fumarate The title compound was obtained in the same manner as in Example 27.

$^1$H-NMR (200 MHzFT, TMS, CD$_3$OD); 1.65–2.00 (4H, m), 2.02–4.00 (23H, complex), 6.67 (2H, s), 6.90–7.60 (8H, complex). MS (FAB, m-NBA) m/z 579, 581→[M+H]$^+$.

EXAMPLE 50

Preparation of Injections

Purified water was added to 30 parts by weight of each compound of the present invention and 18 parts by weight of sodium chloride (100 parts by weight of glucose) so that the total amount might be 2,000 parts by weight. After dissolution was effected, the solution was sterilized by filtration through Millipore Filter-GS type (registered trade name). 2 Grams of the filtrate was dispensed into vials, each of which was plugged and then sealed with a tape by winding the tape tightly round the vial. Thus, injections each containing 30 mg of the compound of the present invention were obtained.

EXAMPLE 51

Preparation of Tablets

Parts by weight of each compound of the present invention, 30 parts by weight of potato starch, 150 parts by weight of crystalline lactose, 108 parts by weight of crystalline cellulose and 2 parts by weight of magnesium stearate were mixed in a twin-cylinder mixer and made into tablets each weighing 60 mg and each containing 2 mg of the compound of the present invention.

The physiological activity of the compounds of the present invention is concretely explained with reference to the following test examples.

TEST EXAMPLE 1

Binding to NK-2 Receptors

Duodenums isolated from Fischer strain male rats were homogenized in 50 mM Tris-hydrochloric acid buffer (pH 7.4) containing saccharose (100 mg/ml) and ethylenediaminetetraacetic acid (1 mM), and the resulting homogenate was centrifuged at 48,000 g and 4° C. for 20 minutes. The pellet thus obtained was washed three times with 10 times as much 50 mM Tris-hydrochloric acid buffer (pH 7.4) containing KCl (300 mM) and ethylenediaminetetraacetic acid (10 mM) as the pellet by volume, and the resulting membrane preparation was suspended in 10 times as much 50 mM Tris-hydrochloric acid buffer (pH 7.4) as the membrane preparation by volume and stored at −80° C. until use. The membrane preparation (20 mg/ml) was incubated together with a radioactive ligand $^{125}$I-neurokinin A (1×10$^{-9}$M) at room temperature for 90 minutes in the presence of each drug or a solvent therefor in 50 mM Tris-hydrochloric acid buffer (pH 7.4) containing bovine serum albumin (10 mg/ml), bacitracin (40 μg/ml), leupeptin (4 μg/ml), chymostatin (50 μg/ml), antipain (1×10$^{-4}$M) and MnCl$_2$ (1 mM). The reaction mixture was filtered by suction through a GE/B filter pretreated with a polyethyleneimine (0.1%), and the filter was washed with 3 ml of 50 mM Tris-hydrochloric acid buffer (pH 7.4) containing MnCl$_2$ (1 mM). Then, radioactivity in the filter was measured with a gamma counter. The 50% inhibitory concentration (IC$_{50}$) of the drug was determined by means of a regression line by considering radioactivity in the presence of Nle10 neurokinin A (4–10) (3×10$^{-6}$M) to be due to nonspecific binding, and measuring the rate of inhibition of specific binding by the drug by carrying out a control experiment using the solvent alone.

The results are shown in Table 1.

TABLE 1

| IC$_{50}$ of drugs in binding of radioactive neurokinin A | |
|---|---|
| Compound | IC50 (M) |
| Compound of Example 25 | 5.6 × 10$^{-8}$ |
| Compound of Example 29 | 5.9 × 10$^{-8}$ |
| Compound of Example 31 | 9.6 × 10$^{-8}$ |
| Compound of Example 33 | 9.4 × 10$^{-8}$ |
| Compound of Example 37 | 9.0 × 10$^{-8}$ |
| Compound of Example 27 | 1.8 × 10$^{-8}$ |
| Compound of Example 39 | 7.0 × 10$^{-8}$ |
| Compound of Example 41 | 3.0 × 10$^{-8}$ |
| Compound of Example 43 | 6.6 × 10$^{-8}$ |

It was found that as is clear from Table 1, the compounds of the present invention inhibit the binding of neurokinin A to NK-2 receptors at a very low concentration, namely, it had a marked inhibitory effect on the binding of the intrinsic stimulating substance to NK-2 receptors.

TEST EXAMPLE 2

Antagonism for NK-2 Receptors

Hartley strain male guinea pigs were killed by a blow on the head and blood-letting, and the tracheas were isolated. Specimens each composed of five slices of the trachea were prepared, and suspended at a tension of 0.5 gw in a magunus bath with an internal volume of 15 ml containing Krebs-Henseleit solution of 37° C. while introducing a mixed gas of 95% O$_2$+5% CO$_2$ into the bath. As the Krebs-Henseleit solution, that containing indomethacin (5×10$^{-6}$) was used for preventing the participation of intrinsic prostaglandins. After confirming the maximum degree of contraction of each specimen by the use of methacholine, a drug or a solvent therefor was added to the solution, followed by incubation for 110 minutes, and neurokinin A (1×10$^{-9}$M) was allowed to act on the specimen. Phosphoramidon (1×10$^{-5}$M) for inhibiting the degradation of neurokinin A and (±)CP-96345 (3×10$^{-7}$M) for preventing the participation of NK-1 receptors were added 30 minutes and 20 minutes, respectively, before the addition of neurokinin A. The degree of contraction due to neurokinin A was converted to the percentage based on the maximum degree of contraction of the specimen, and then the rate of inhibition by the drug was determined relative to the percentage of contraction of the other specimen used in the case of adding the solvent.

The results are shown in Table 2.

TABLE 2

Inhibition of a drug on neurokinin A induced contraction

| Compound | Concentration (M) | Inhibition rate (%) |
|---|---|---|
| Compound of Example 25 | $5 \times 10^{-9}$ | 89.1 |

It was found that as is clear from Table 2, the compound of the present invention has a marked inhibitory effect on the contraction due to neurokinin A at a very low concentration, namely, said compound shows a very strong antagonism for NK-2 receptors.

TEST EXAMPLE 3

Antagonism for NK-1 Receptor

Hartley strain male guinea pigs were killed by a blow on the head and blood-letting, and the ileums were isolated. A specimen of about 3 cm in length was prepared and then suspended at a tension of 0.5 gw in a 15 magunus bath with an internal volume of 15 ml containing Krebs-Henseleit solution of 37° C. while introducing a mixed gas of 95% $O_2$+5% $CO_2$ into the bath. As the Krebs-Henseleit solution, that containing atropine ($1 \times 10^{-6}$M) and indomethacin ($5 \times 10^{-6}$M) was used for preventing the participation of intrinsic acetylcholine and prostaglandins. Methylsubstance P ($1 \times 10^{-9}$M), a specific stimulating agent for NK-1 receptors were repeatedly allowed to act on the specimen at intervals of 40 minutes. After the percentage of contraction due to methylsubstance P became constant, a drug was added to the solution to each of various concentrations, followed by incubation for 35 minutes, and methylsubstance P was allowed to act on the specimen again. The rate of inhibition by the drug was determined relative to the percentage of contraction immediately before the addition of the drug, and the 50% inhibitory concentration ($IC_{50}$) of the drug was determined by means of a regression line.

TABLE 3

$IC_{50}$ of a drug on methylsubstance P induced contraction

| Compound | IC50 (M) |
|---|---|
| Compound of Example 25 | $4.7 \times 10^{-7}$ |

It was found that as is clear from Table 3, the compound of the present invention shows not only antagonism for NK-2 receptors but also antagonism for NK-1 receptors.

TEST EXAMPLE 4

Antagonism for NK-3 receptors

Hartley strain male guinea pigs were killed by a blow on the head and blood-letting, and the ileums were isolated. A specimen of about 3 cm in length was prepared and then suspended at a tension of 0.5 gw in a magunus bath with an internal volume of 15 ml containing Krebs-Henseleit solution of 37° C. while introducing a mixed gas of 95% $O_2$ and 5% $CO_2$ into the bath. As the Krebs-Henseleit solution, that containing atropine ($1 \times 10^{-6}$M) and indomethacin ($5 \times 10^{-6}$M) was used for preventing the participation of intrinsic acetylcholine and prostaglandins. Senctide ($1 \times 10^{-9}$M), a specific stimulating agent for NK-3 receptors was repeatedly allowed to act on the specimen at intervals of 50 minutes. After the percentage of contraction due to senctide became constant, a drug was added to the solution to each of various concentrations, followed by incubation for 35 minutes, and senctide was allowed to act on the specimen again. The rate of inhibition by the drug was determined relative to the percentage of contraction immediately before the addition of the drug, and the 50% inhibitory concentration ($IC_{50}$) was determined by means of a regression line.

The results are shown in Table 4.

TABLE 4

$IC_{50}$ of a drug on senctide induced contraction

| Compound | IC50 (M) |
|---|---|
| Compound of Example 25 | $1.8 \times 10^{-7}$ |

It was found that as is clear from Table 4, the compound of the present invention also shows antagonism for NK-3 receptors.

TEST EXAMPLE 5

Inhibitory Effect on Bronchoconstriction

There were used non-treated Hartley strain male guinea pigs and Hartley strain male guinea pigs received to active sensitization by subcutaneous administration of 30 mg/kg of ovalbumin 14 to 21 days before. The guinea pigs were anesthetized with pentobarbital and a tube was inserted into the trachea of each guinea pig. The guinea pigs were subjected to positive pressure respiration by means of an artificial respiratory apparatus at 10 ml/kg and 60 times/minute. The pressure in the edge of the tube in the trachea was measured as an indication of bronchoconstriction. Spontaneous respiration was inhibited by administering succinylcholine. The non-treated guinea pigs were repeatedly and intravenously injected with 2 nmol/kg of Nle10 neurokinin A (4–10), a specific stimulating agent for NK-2 receptors at intervals of 10 minutes. After the bronchoconstriction thus caused became stable, each drug was administered intravenously, orally or in duodenum. Nle10 neurokinin A (4–10) was intravenously injected again 3 minutes after the intravenous administration or 50 minutes after the oral administration or the administration in duodenum. The rate of inhibition by the drug was determined relative to the bronchoconstriction before the drug administration.

To the guinea pigs received to active sensitization, 4.6 μmol/kg of phosphoramidon was intravenously administered, and 15 minutes after the administration, these guinea pigs were allowed to inhale for 2 minutes an aerosol of an antigen ovalbumin solution (2 mg/ml) produced with an ultrasonic nebulizer, to cause bronchoconstriction. A drug or a solvent therefor was orally administered 50 minutes before the antigen inhalation. The inhibition rate of the drug-treated group was determined relative to the bronchoconstriction of the solvent-treated group measured 8 minutes after the antigen inhalation.

The results are shown in Table 5.

TABLE 5

Inhibitory effect of drugs on the bronchoconstriction caused by stimulation of an NK-2 receptor or inhalation of an antigen

| Compound | Dose (μmol/kg) | Administration route | Inhibition (rate) (%) | |
|---|---|---|---|---|
| | | | Stimulation of NK-2 receptors | Inhalation of antigen |
| Compound of Example 25 | 1 | intravenous | 94.2 | |
| Compound of Example 29 | 0.6 | intravenous | 100.0 | |
| Compound of Example 31 | 1 | intravenous | 100.0 | |
| Compound of Example 33 | 1 | intravenous | 57.5 | |
| Compound of Example 37 | 1 | intravenous | 97.5 | |
| Compound of Example 27 | 0.5 | intravenous | 100.0 | |
| Compound of Example 39 | 0.5 | intravenous | 70.0 | |
| Compound of Example 41 | 0.5 | intravenous | 97.0 | |
| Compound of Example 43 | 0.5 | intravenous | 86.2 | |
| Compound of Example 25 | 8 | oral | 67.2 | |
| Compound of Example 29 | 8 | oral | 43.5 | |
| Compound of Example 31 | 8 | oral | 53.5 | |
| Compound of Example 27 | 8 | oral | 81.5 | |
| Compound of Example 41 | 5 | in duodenum | 62.0 | |
| Compound of Example 25 | 10 | oral | | 54.1 |

It was found that as is clear from Table 5, the compounds of the present invention inhibit the bronchoconstriction at a very low dose, namely, they have a marked antiasthmatic effect.

TEST EXAMPLE 6

Toxic Effect on Mouse

The toxicity of the compounds of the present invention was investigated.

TABLE 6

Toxicity of drugs intravenously administered

| Compound | Dose (μmol/kg) | Toxicity |
|---|---|---|
| Compound of Example 25 | 22 | None |
| | 65 | None |
| Compound of Example 27 | 65 | None |

It was found that as is clear from Table 6, the compounds of the present invention have such a very small side effect that they are not toxic even when administered at a high dose.

As described above, the compound of the present invention shows an excellent antagonism for tachykinin receptors and are thoroughly satisfactory in safety. It was also confirmed that in addition to having the above effect, the compound of the present invention exerts the effect very immediately and is so excellent in safety that it does not modify the higher-order structure of an organ (for example, bronchus).

INDUSTRIAL APPLICABILITY

According to the present invention, there are provided novel naphthyridine derivatives for preventing or treating various symptoms in which tachykinins participate and all tachykinin-dependent diseases such as diseases of respiratory organs. In addition, according to the present invention, a process for production of these novel naphthyridine derivatives is provided. Furthermore, according to the present invention, there is provided a pharmaceutical composition for mammals containing the novel naphthyridine derivative of the present invention which is effective against the the above-mentioned symptoms and diseases.

What is claimed is:

1. A naphthyridine compound represented by the following general formula (1):

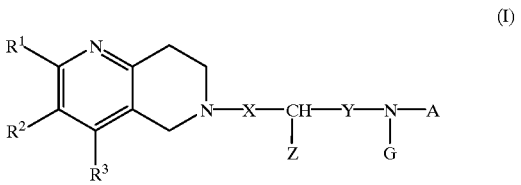

(I)

wherein $R^3$ is selected from the group consisting of hydrogen atom; lower alkyl groups; halogeno-lower-alkyl groups; phenyl groups; lower alkoxy groups; hydroxyl group; amino group; halogen atoms; trifluoromethyl group; amino protecting groups represented by $NR_aCOR_b$ wherein $R_a$ and $R_b$ are independently a hydrogen atom, a lower alkyl group, a cycloalkyl group or a phenyl group; lower acyloxy groups; nitro group; cyano group; amino protecting groups represented by $NR_aR_b$ wherein $R_a$ and $R_b$ are independently a hydrogen atom, a lower alkyl group, a cycloalkyl group or a phenyl group; lower alkylsulfonylamino groups; lower alkoxycarbonyl groups; carboxyl group; lower acyl groups; carbamoyl group; aminocarbonyl groups represented by $CONR_aR_b$ wherein $R_a$ and $R_b$ are independently a hydrogen atom, a lower alkyl group, a cycloalkyl group or a phenyl group; amninocarbonyl groups represented by COJ wherein J is a substituted or unsubstituted pyrrolidino, piperidino, piperazino, homopiperazino or morpholino group; lower alkylsulfonyl groups; amino protecting groups represented by $NR_aCOOR_b$ wherein $R_a$ and $R_b$ are independently a hydrogen atom, a lower alkyl group, a cycloalkyl group or a phenyl group; and hydroxyl-lower-alkyl groups, a combination of $R^1$ and $R^2$ forms through the saturated or unsaturated carbon-carbon bond a cyclic group which may contain 1 to 3 heteroatoms selected from nitrogen atom, oxygen atom and sulfur atom and may have a substituent selected from the group consisting of lower alkyl groups; phenyl group; lower alkoxy groups; hydroxyl group; amino group; halogen atoms; trifluoromethyl group; amino protecting groups represented by $NR_aCOR_b$ wherein $R_a$ and $R_b$ are independently a hydrogen atom, a lower alkyl group, a cycloalkyl group or a phenyl group; lower acyloxy groups; nitro group; cyano group; amino protecting groups represented by $NR_aR_b$ wherein $R_a$ and $R_b$ are independently a hydrogen atom, a lower alkyl group, a cycloalkyl group or a phenyl group; lower alkylsulfonylamino groups; lower alkoxycarbonyl groups; carboxyl group; lower acyl groups; carbamoyl group; aminocarbonyl groups represented by $CONR_aR_b$ wherein $R_a$ and $R_b$ are independently a hydrogen atom, a lower alkyl group, a cycloalkyl group or a phenyl group; aminocarbonyl groups represented by COJ wherein J is a substituted or unsubstituted pyrrolidino, piperidino, piperazino, homopiperazino or morpholino group; lower alkylsulfonyl groups; oxo group; amino protecting groups represented by $NR_aCOOR_b$ wherein $R_a$ and $R_b$ are independently a hydrogen atom, a lower alkyl group, a cycloalkyl group or a phenyl group; and hydroxyl-lower-alkyl groups, X and Y are independently a methylene chain represented by —$(CH_2)_n$— wherein n is 0 to 3, Z is a phenyl group, a phenylalkyl group or a phenylalkenyl group, each of which may have one or more substituents selected from the group consisting of lower alkyl groups, phenyl group, lower alkoxy groups, hydroxyl group, amino group, halogen atoms and trifluoromethyl group, A is a hydrogen atom, a lower alkyl group or a lower alkoxy group, and G is a hydrogen atom, a lower alkyl group, a lower alkoxy group, a phenylalkyl group or an acyl group represented by —C(=O)XZ, —C(=O)CH($R^1$)(Z) or —C(=O)C($R^1$)($R^2$)(Z) wherein X, Z, $R^1$ and $R^2$ are as defined above, or a pharmacologically acceptable salt thereof.

2. A compound or a pharmacologically acceptable salt thereof according to claim 1, wherein $R^3$ is a hydrogen atom, a lower alkyl group, a phenyl group, an amino group, a halogen atom, an amino protecting group represented by $NR_aCOR_b$ wherein $R_a$ and $R_b$ are as defined above, a lower alkoxycarbonyl group, a carboxyl group, a carbamoyl group, an amino protecting group represented by $NR_aCOOR_b$ wherein $R_a$ and $R_b$ are as defined above, or a hydroxyl-lower-alkyl group, a combination of $R^1$ and $R^2$ forms a cyclic group through the saturated or unsaturated carbon-carbon bond, X is a methylene chain represented by —$(CH_2)_2$—; Y is a methylene chain represented by —$CH_2$—; and Z is a phenyl group which may have 1, 2 or 3 substituents selected from lower alkyl groups and halogen atoms.

3. A compound or a pharmacologically acceptable salt thereof according to claim 1, wherein $R^3$ is a hydrogen atom, a lower alkyl group, a phenyl group, an amino group, a halogen atom, an amino protector represented by $NR_aCOR_b$ wherein $R_a$ and $R_b$ are as defined above, a lower alkoxycarbonyl group, a carboxyl group, a carbamoyl group, an amino protecting group represented by $NR_aCOOR_b$ wherein $R_a$ and $R_b$ are as defined above, or a hydroxyl-lower-alkyl group, $R^1$ and $R^2$ are taken together to form a $C_2$–$C_5$ alkylene group or a $C_2$–$C_5$ alkenylene group, Z is a phenyl group which may have 1, 2 or 3 substituents selected from halogen atoms; A is a hydrogen atom, a $C_1$–$C_4$ lower alkyl group or a $C_1$–$C_4$ lower alkoxy group; and G is a benzoyl group which may have 1, 2 or 3 substituents selected from halogen atoms and lower alkoxy groups.

4. A compound or a pharmacologically acceptable salt thereof according to claim 1, wherein $R^3$ is a hydrogen atom, a lower alkyl group, a phenyl group, an amino group, an amino protecting group represented by $NR_aCOR_b$ wherein $R_a$ and $R_b$ are as defined above, a lower alkoxycarbonyl group, a carbamoyl group, or an amino protecting group represented by $NR_aCOOR_b$ wherein $R_a$ and $R_b$ are as defined above, $R^1$ and $R^2$ are taken together to form a $C_2$–$C_5$ alkylene group or a $C_2$–$C_5$ alkenylene group, Z is a phenyl group which may have 1, 2 or 3 substituents selected from halogen atoms; A is a hydrogen atom, a $C_1$–$C_4$ lower alkyl group or a $C_1$–$C_4$ lower alkoxy group; and G is a benzoyl group which may have 1, 2 or 3 substituents selected from halogen atoms and lower alkoxy groups.

5. A compound or a pharmacologically acceptable salt thereof according to claim 1, wherein $R^3$ is a hydrogen atom, a lower alkyl group, an amino protecting group represented by $NR_aCOOR_b$ wherein $R_a$ and $R_b$ are as defined above, or an amino protecting group represented by $NR_aCOOR_b$ wherein $R_a$ and $R_b$ are as defined above, $R^1$ and $R^2$ are taken together to form a $C_2$–$C_5$ alkylene group or a $C_2$–$C_5$ alkenylene group, Z is a phenyl group which may have 1, 2 or 3 substituents selected from halogen atoms; A is a hydrogen atom, a $C_1$–$C_4$ lower alkyl group or a $C_1$–$C_4$ lower alkoxy group; and G is a benzoyl group which may have 1, 2 or 3 substituents selected from halogen atoms and lower alkoxy groups.

6. A compound or a pharmacologically acceptable salt thereof according to claim 1, wherein $R^1$ and $R^2$ are taken together to form a $C_2$–$C_5$ alkylene group or a $C_2$–$C_5$ alkenylene group; $R^3$ is a hydrogen atom, a lower alkyl group, a phenyl group, a lower alkoxycarbonyl group, a hydroxyl-lower-alkyl group, an amino protecting group represented by $NR_aCOR_b$ wherein $R_a$ and $R_b$ are as defined above, or an amino protecting group represented by $NR_aCOOR_b$ wherein $R_a$ and $R_b$ are as defined above, Z is a phenyl group which may have 1, 2 or 3 substituents selected from halogen atoms; A is a hydrogen atom, a $C_1$–$C_4$ lower alkyl group or a $C_1$–$C_4$ lower alkoxy group; and G is a benzoyl group which may have 1, 2 or 3 substituents selected from halogen atom and lower. alkoxy groups.

7. A compound or a pharmacologically acceptable salt thereof according to claim 1, which is selected from the following compounds:

2-[(±)-4-(N-benzoyl-N-methyl)amino-3-(3,4-dichlorophenyl)butyl]-1,2,3,4,6,7,8,9-octahydro-benzo[b][1,6]naphthyridine or a pharmacologically acceptable salt thereof, 2-[(±)-4-(N-benzoyl-N-methyl)amino-3-(3,4-dichlorophenyl)butyl]-1,2,3,4-tetrahydro-benzo[b][1,6]-naphthyridine-10-carboxamide or a pharmacologically acceptable salt thereof, 2-[(±)-4-(N-benzoyl-N-methyl)amino-3-(3,4-dichlorophenyl)butyl]-10-methoxycarbonyl-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-1,2,3,4-tetrahydro-benzo[b][1,6]-naphthyridine-10-carboxylic acid or a pharmacologically acceptable salt thereof, 10-amino-2-[(±)-4-(N-benzoyl-N-methyl) amino-3-(3,4-dichlorophenyl)butyl]-1,2,3,4-tetrahydro-benzo[b][1,6]naphthyridine or a pharmacologically acceptable salt thereof, 2-[(±)-4-(N-benzoyl-N-methyl) amino-3-(3,4-dichlorophenyl)butyl]-10-hydroxymethyl-1,2,3,4-tetrahydro-benzo[b][1,6]naphthyridine or a pharmacologically acceptable salt thereof, 2-[(±)-4-(N-benzoyl-N-methyl) amino-3-(3,4-dichlorophenyl)butyl]-10-acetylamino-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-10-phenyl-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-10-methoxycarbonylamino-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-10-(N-methyl-N- methoxycarbonyl)-amino-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-10-chloro-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-10-benzoylamino-1,2,3,4-tetrahydro-benzo[b][1,6]naphthyridine or a pharmacologically acceptable salt thereof, 2-[(±)-4-(N-benzoyl-N-methyl)amino-3-(3,4-dichlorophenyl)butyl]-10-acetylamino-1,2,3,4,6,7,8,9-octahydro-benzo[b][1,6]naphthyridine or a pharmacologically acceptable salt thereof, 2-[(±)-4-(N-benzoyl-N-methyl)amino-3-(3,4-difluorophenyl)butyl]-1,2,3,4,6,7,8,9-octahydro-benzo[b][1,6]naphthyridine or a pharmacologically acceptable salt thereof, and 2-[(±)-4-(N-benzoyl-N-methyl)amino-3-(3,4-difluorophenyl)butyl]-10-acetylamino-1,2,3,4-tetrahydro-benzo[b][1,6]naphthyridine or a pharmacologically acceptable salt thereof.

8. A compound or a pharmacologically acceptable salt thereof according to claim 1, which is selected from the following compounds:

2-[(−)-4-(N-benzoyl-N-methyl)amino-3-(3,4-dichlorophenyl)butyl)-1,2,3,4,6,7,8,9-octahydro-benzo[b][1,6]naphthyridine or a pharmacologically acceptable salt thereof, 2-[(−)-4-(N-benzoyl-N-methyl)amino-3-(3,4-dichlorophenyl)butyl]-1,2,3,4-tetrahydro-benzo[b][1,6]-naphthyridine-10-carboxamide or a pharmacologically acceptable salt thereof, 2-[(−)-4-(N-benzoyl-N-methyl)amino-3-(3,4-dichlorophenyl)butyl]-10-methoxycarbonyl-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-1,2,3,4-tetrahydro-benzo[b][1,6]-naphthyridine-10-carboxylic acid or a pharmacologically acceptable salt thereof, 10-amino-2-[(−)-4-(N-benzoyl-N-methyl)amino-3-(3,4-dichlorophenyl)butyl]-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-hydroxymethyl-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-acetylamino-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-phenyl-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-methoxycarbonylamino-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-(N-methyl-N-methoxycarbonyl)-amino-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-chloro-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-benzoylamino-1,2,3,4-tetrahydro-benzo[b][1,6]naphthyridine or a pharmacologically acceptable salt thereof, 2-[(−)-4-(N-benzoyl-N-methyl)amino-3-(3,4-dichlorophenyl)butyl]-10-acetylamino-1,2,3,4,6,7,8,9-octahydro-benzo[b][1,6]naphthyridine or a pharmacologically acceptable salt thereof, 2-[(−)-4-(N-benzoyl-N-methyl)amino-3-(3,4-difluorophenyl)butyl]-1,2,3,4,6,7,8,9-octahydro-benzo[b][1,6]naphthyridine or a pharmacologically acceptable salt thereof, and 2-[(−)-4-(N-benzoyl-N-methyl)amino-3-(3,4-difluorophenyl)butyl]-10-acetylamino-1,2,3,4-tetrahydro-benzo[b][1,6]naphthyridine or a pharmacologically acceptable salt thereof.

9. A process for producing a compound according to any one of claims 1 to 8, which comprises carrying out reductive alkylation by using a 5,6,7,8-tetrahydro-1,6-naphthyridine represented by the following general formula (2):

(2)

wherein $R^1$, $R^2$ and $R^3$ are as defined above, and an aldehyde represented by the following general formula (3):

(3)

wherein X, Y, Z, A and G are as defined above.

10. A process for producing a compound according to any one of claims 1 to 8, which comprises N-alkylating a compound represented by the following general formula (2):

(2)

wherein $R^1$, $R^2$ and $R^3$ are as defined above, with a compound represented by the following general formula (4):

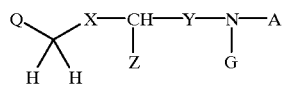 (4)

wherein X, Y, Z, A and G are as defined above, Q is a halogen atom or a $R_4SO_2O$— group wherein $R_4$ is a lower alkyl group, an aryl group or a trifluoromethyl group.

11. A pharmaceutical composition comprising a compound or a pharmacologically acceptable salt thereof according to any one of claims 1 to 8, and a pharmaceutically acceptable diluent or carrier.

12. A pharmaceutical composition for treatment of bronchitis, pollakiuria, urinary incontinence and colitis, comprising a compound or a pharmacologically acceptable salt thereof according to any one of claims 1 to 8 as an active ingredient.

13. A pharmaceutical composition for treatment of asthma comprising a compound or a pharmacologically acceptable salt thereof according to any one of claims 1 to 8 as an active ingredient.

14. A method for treating diseases selected from the group consisting of asthma, bronchitis, pulmonary obstructive disease, pollakiuria, urinary incontinence, anxiety, irritable bowel syndrome, migraine, pain, allergy, inflammation and colitis in which tachykinin receptors participate, which comprises administering to a patient a compound or a pharmacologically acceptable salt thereof according to any one of claim 1 to 8.

15. A method for antagonizing at tachykinin receptors, which comprises administering to a patient a compound or a pharmaceutically acceptable salt thereof according to any one of claims 1 to 8.

16. A method for antagonizing at neurokinin-2 receptors, which comprises administering to a patient a compound or a pharmaceutically acceptable salt thereof according to any one of claims 1 to 8.

* * * * *